(12) United States Patent
Mao et al.

(10) Patent No.: US 10,738,272 B2
(45) Date of Patent: Aug. 11, 2020

(54) HEATING ASSEMBLY FOR A BIOREACTOR AND AN ASSOCIATED METHOD THEREOF

(71) Applicant: General Electric Company, Schenectady, NY (US)

(72) Inventors: Ying Mao, Cohoes, NY (US); Weston Blaine Griffin, Niskayuna, NY (US); Younkoo Jeong, Clifton Park, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 511 days.

(21) Appl. No.: 15/193,485

(22) Filed: Jun. 27, 2016

(65) Prior Publication Data
US 2017/0369832 A1    Dec. 28, 2017

(51) Int. Cl.
| | |
|---|---|
| *C12M 1/02* | (2006.01) |
| *C12M 1/36* | (2006.01) |
| *C12M 1/00* | (2006.01) |
| *C12M 3/00* | (2006.01) |
| *C12Q 3/00* | (2006.01) |

(52) U.S. Cl.
CPC ............ *C12M 41/22* (2013.01); *C12M 23/02* (2013.01); *C12M 23/48* (2013.01); *C12M 41/48* (2013.01); *C12Q 3/00* (2013.01)

(58) Field of Classification Search
CPC ...... C12M 23/48; C12M 41/12; C12M 41/22; C12M 41/48; C12Q 3/00
See application file for complete search history.

(56) References Cited

U.S. PATENT DOCUMENTS

| | | | |
|---|---|---|---|
| 8,304,232 B2 | 11/2012 | Morgan et al. | |
| 9,121,006 B2 | 9/2015 | Denoual | |
| 2002/0096512 A1* | 7/2002 | Abbott | B29C 45/73 219/543 |
| 2004/0121453 A1 | 6/2004 | Rao | |
| 2005/0089993 A1 | 4/2005 | Boccazzi et al. | |
| 2010/0009335 A1 | 1/2010 | Joseph et al. | |
| 2010/0075405 A1 | 3/2010 | Broadley | |
| 2013/0177972 A1 | 7/2013 | Green et al. | |
| 2013/0260421 A1* | 10/2013 | Yamaguchi | B01L 7/52 435/91.2 |
| 2013/0288346 A1 | 10/2013 | Tuohey et al. | |

FOREIGN PATENT DOCUMENTS

| | | |
|---|---|---|
| WO | 2008118500 A1 | 10/2008 |
| WO | 2013106809 A1 | 7/2013 |

* cited by examiner

*Primary Examiner* — Gautam Prakash
*Assistant Examiner* — Lydia Edwards
(74) *Attorney, Agent, or Firm* — Culhane Meadows PLLC; Jeff B. Vockrodt

(57) ABSTRACT

A heating assembly for a bioreactor is disclosed. The heating assembly includes a holder having a plurality of segments coupled to each other to define a unitary structure and a heating component coupled to at least one segment of the plurality of segments. The unitary structure includes a top end, a bottom end, and a side wall. The side wall extends between the top end and the bottom end and along a circumferential direction of the heating assembly to define a cavity. At least a portion of the unitary structure has a gradually varied perimeter along a direction perpendicular to a plane which intersects the side wall and is parallel to the top end and the bottom end.

12 Claims, 20 Drawing Sheets

HEATING ASSEMBLY FOR A BIOREACTOR AND AN ASSOCIATED METHOD THEREOF

BACKGROUND

Embodiments of the present invention relate to bioreactors used for culturing cells, and more specifically, to a heating assembly for a bioreactor and an associated method thereof.

Cell culture technology has advanced significantly over the last few decades and has contributed immensely in therapeutic applications, clinical studies, pharmaceutical research and development, and bioprocess industry. To meet an increasing demand of biomolecules, for example, protein or viable cells or enzymes or metabolic products for therapeutic applications or non-therapeutic applications, large scale manufacturing facilities and high throughput technological developments for culturing large quantities of cells are highly desirable.

For large scale operations, a seed train expansion process is typically followed to scale up the cell culture production from a small volume to a large volume. The seed train expansion process is generally initiated by inoculating cryopreserved cells into a small culture device such as T-flasks or petri-plates. The cultured cells from such small culture device are then transferred to a small suspension culture vessel for further culturing of cells. As the cells grow to a predefined quantity within such smaller culture vessel, the cells are further transferred to large suspension culture vessel filled with more cell-culture media. Such a process of growing and transferring the cells between the culture vessels requires frequent manual intervention, skilled operator for managing the seed train expansion process, and use of a plurality of culture vessels, thereby resulting in increased probability of introducing contamination into the cell culture.

Multi-scale bioreactors having a complex structure and capable of supporting a large volume range are used as an alternative mechanism for culturing cells. In such a bioreactor, a single culture vessel is configured to receive an inoculation of starter cells. Further, the cell-culture media is added continuously to the culture vessel including the starter cells to facilitate scaling up of the culture volume in a plurality of steps in the single bioreactor vessel. However, maintaining various parameters such as potential of Hydrogen (pH), dissolved oxygen (DO), and temperature within the multi-scale bioreactor is difficult. Specifically, maintaining a temperature condition or temperature regime of the cell-culture media within a culture vessel of such bioreactor is challenging and difficult. This is further accentuated by the challenge of preventing condensation of water on side walls of the head space of the culture vessel which may result in altering osmolality of the bioreactor.

Accordingly, there is a need for an enhanced heating assembly for a bioreactor and an associated method for heating a culture vessel of the bioreactor.

BRIEF DESCRIPTION

In accordance with one exemplary embodiment, a heating assembly for a bioreactor. The heating assembly includes a holder having a plurality of segments coupled to each other to define a unitary structure and a heating component coupled to at least one segment of the plurality of segments. The unitary structure includes a top end, a bottom end, and a side wall. The side wall extends between the top end and the bottom end and along a circumferential direction of the heating assembly to define a cavity. At least a portion of the unitary structure has a gradually varied perimeter along a direction perpendicular to a plane which intersects the side wall and is parallel to the top end and the bottom end.

In accordance with another exemplary embodiment, a bioreactor is disclosed. The bioreactor includes a culture vessel used for culturing a plurality of cells in a cell-culture media and a heating assembly coupled to the culture vessel. The heating assembly includes a holder having a plurality of segments coupled to each other to define a unitary structure and a heating component coupled to at least one segment of the plurality of segments. The unitary structure includes a top end, a bottom end, and a side wall. The side wall extends between the top end and the bottom end and along a circumferential direction of the heating assembly to define a cavity. At least a portion of the unitary structure has a gradually varied perimeter along a direction perpendicular to a plane which intersects the side wall and is parallel to the top end and the bottom end.

In accordance with another exemplary embodiment, a method for heating a bioreactor is disclosed. The method involves receiving a cell-culture media including a plurality of cells in a culture vessel of a bioreactor. The method further involves heating the cell-culture media using a heating assembly coupled to the culture vessel. The heating assembly includes a holder having a plurality of segments coupled to each other to define a unitary structure and a heating component coupled to at least one segment of the plurality of segments. The unitary structure includes a top end, a bottom end, and a side wall. The side wall extends between the top end and the bottom end and along a circumferential direction of the heating assembly to define a cavity. At least a portion of the unitary structure has a gradually varied perimeter along a direction perpendicular to a plane which intersects the side wall and is parallel to the top end and the bottom end. Further, the method involves establishing a temperature gradient along the culture vessel from the top end to the bottom end, using the heating assembly for culturing the plurality of cells.

DRAWINGS

These and other features and aspects of embodiments of the present invention will become better understood when the following detailed description is read with reference to the accompanying drawings in which like characters represent like parts throughout the drawings, wherein.

DETAILED DESCRIPTION

Embodiments of the present invention discussed herein relate to a heating assembly of a bioreactor used for culturing a plurality of cells. In certain embodiments, the heating assembly is configured to receive and hold a culture vessel of the bioreactor. In such embodiments, the heating assembly is configured to establish a temperature gradient along the culture vessel to provide a conducive environment for culturing the plurality of cells. In one embodiment, the heating assembly includes a holder and a heating component. The holder includes a plurality of segments coupled to each other to define a unitary structure. In certain embodiments, the plurality of segments may be stacked along an axial direction of the heating assembly or disposed adjacent to each other along the circumferential direction of the heating assembly, to define the unitary structure.

Figure 1:
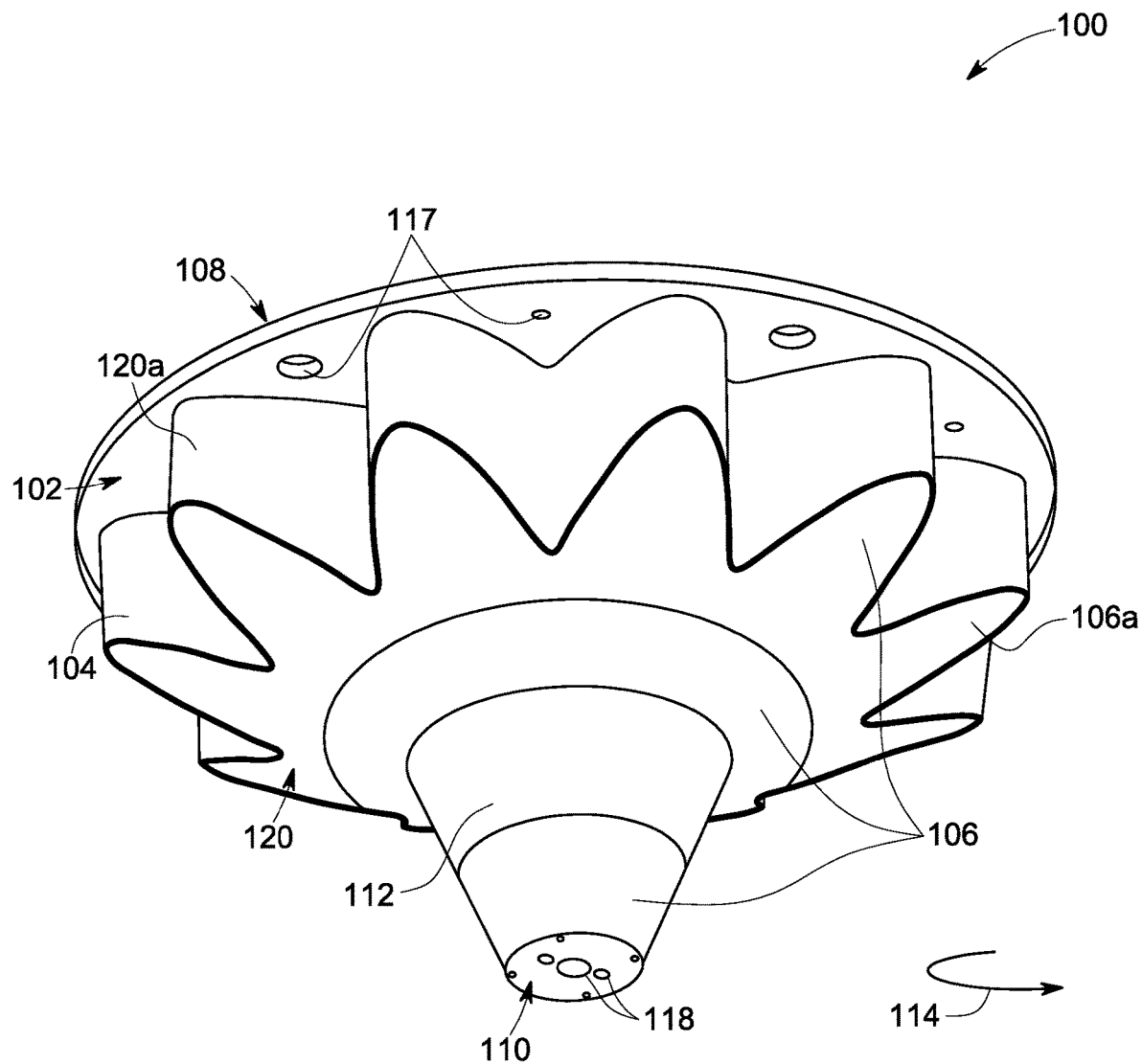
FIG. 1 is a side perspective view of a heating assembly in accordance with one exemplary embodiment.

FIG. 1 illustrates a side perspective view of a heating assembly 100 for a bioreactor in accordance with one exemplary embodiment. The heating assembly 100 includes a holder 102 and a heating component 104.

In the illustrated embodiment, the holder 102 includes a plurality of segments 106 coupled to each other to define a unitary structure. It should be noted herein that the terms "a unitary structure" and "a holder" may be used interchangeably. In one embodiment, the unitary structure 102 has a flower-shaped structure. In another embodiment, the unitary structure 102 has a conical shaped structure. The unitary structure 102 includes a top end 108, a bottom end 110, and a side wall 112. The side wall 112 extends between the top end 108 and the bottom end 110 and along a circumferential direction 114 of the heating assembly 100 to define a cavity (not shown in FIG. 1). The unitary structure 102 includes an outer peripheral surface 120 and an inner peripheral surface (not shown in FIG. 1). The top end 108 includes a plurality of holes 117 for securing the heating assembly 100 to a holding equipment (not shown in FIG. 1) via a suitable securing mechanism such as screw elements. The bottom end 110 of unitary structure 102 include a plurality of holes 118 for holding one or more temperature sensors (not shown in FIG. 1) configured to generate inputs signals representative of temperature of at least one of the plurality of segments 106 and a cell-culture media filled within a culture vessel (not shown in FIG. 1) held by the holder 102. In one embodiment, the unitary structure 102 is made of metal such as aluminum, copper, and the like. In another embodiment, the unitary structure 102 is made of heat conducting non-metallic material. In certain embodiments, the unitary structure 102 is manufactured using a 3D printing technique, a molding technique, machining, die casting, and the like.

The heating component 104 is coupled to at least one segment of the plurality of segments 106. In the illustrated embodiment, the heating component 104 is coupled to a top segment 106a of the plurality of segments 106. In one embodiment, the heating component 104 is made of thin sheet of metal made of aluminum, copper, and the like. In the illustrated embodiment, the heating component 104 is disposed on an outer peripheral surface portion 120a of the top segment 106a. Specifically, the heating component 104 extends along the circumferential direction 114 of the heating assembly 100. The heating component 104 may be coupled to the top segment 106a via a suitable mechanism such as glue. The heating component 104 conforms to the shape of the top segment 106a. The heating component is coupled to a power source (not shown in FIG. 1) configured to supply electric power to the heating component 104 to heat the culture vessel. Other non-limiting examples of the heating component 104 may include a non-contact heater such as an infrared (IR) heater, an elastic vessel with temperature-regulated fluid circulating within the culture vessel, and the like. The heating component 104 is in good thermal contact with the unitary structure 102 with a tight tolerance. In one example, the heating component 104 may have a flexible and conformable structure. In a non-limiting example, the heating component 104 may be a thin film heater.

Figure 2:
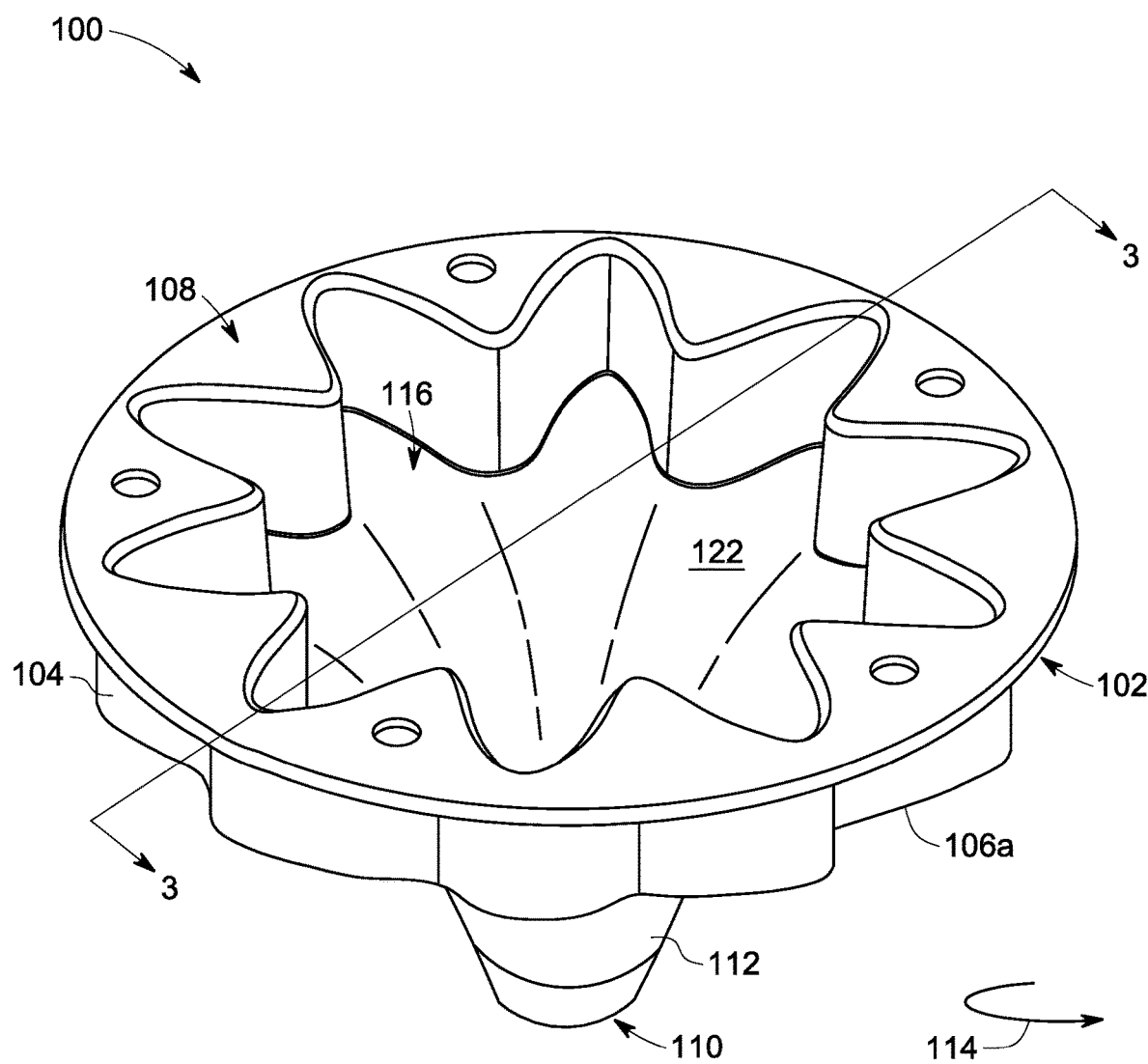
FIG. 2 is a top perspective view of the heating assembly in accordance with the exemplary embodiment of FIG. 1.

FIG. 2 illustrates a top perspective view of the heating assembly 100 in accordance with the exemplary embodiment of FIG. 1. In the illustrated embodiment, the side wall 112 extends between the top end 108 and the bottom end 110 and along the circumferential direction 114 of the heating assembly 100 to define a cavity 116. The unitary structure 102 is configured to receive the culture vessel (not shown in FIG. 2) in the cavity 116. The unitary structure 102 has an inner peripheral surface 122 which conforms to an outer peripheral surface (not shown in FIG. 2) of the culture vessel.

Figure 3:
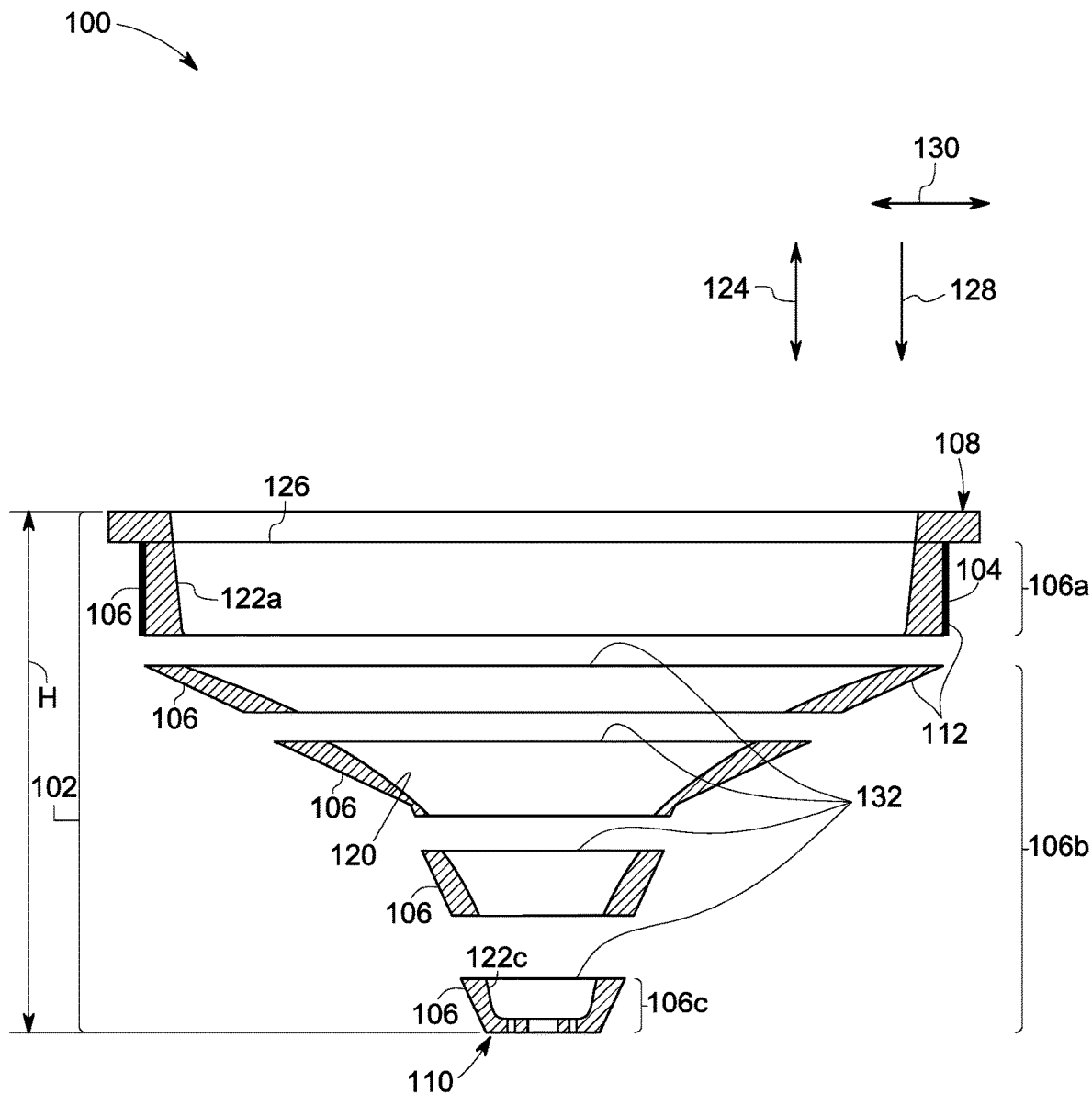
FIG. 3 is an exploded sectional view of the heating assembly taken along line 3-3 in accordance with the exemplary embodiment of FIG. 2.

FIG. 3 illustrates an exploded sectional view of the heating assembly 100 taken along line 3-3 in accordance with the exemplary embodiment of FIG. 2. The holder 102 includes the plurality of segments 106 coupled to each other to define the unitary structure. In the illustrated embodiment, the plurality of segments 106 is stacked along an axial direction 124 of the heating assembly 100. The unitary structure 102 includes the top segment 106a having a uniform perimeter 126 along a direction 128 perpendicular to a plane 130. The plane 130 intersects the outer peripheral surface 120 of the side wall 112 and is parallel to the top end 108 and the bottom end 110. The top segment 106a is coupled to the top end 108. The unitary structure 102 further includes a remaining portion 106b of the unitary structure 102 having a gradually varied perimeter 132 along the direction 128 perpendicular to the plane 130.

The heating component 104 is coupled to the top segment 106a and is configured to generate a temperature gradient along the axial direction 124 of the heating assembly 100. In one embodiment, the temperature gradient is established from top end 108 to the bottom end 110 along the axial direction 124 of the heating assembly 100 to prevent water condensation along an inner peripheral surface of the culture vessel. The generation of temperature gradient is explained in greater detail with reference to subsequent figures.

In one embodiment, the temperature is maintained approximately at about 38 degrees Celsius along an inner peripheral surface portion 122a of the top segment 106a and at about 37 degrees Celsius along an inner peripheral surface portion 122c of a bottom segment 106c which is coupled to the bottom end 110. The temperature gradient enables to maintain a temperature of an inner peripheral surface of the culture vessel above a temperature of the cell-culture media disposed within a bottom segment 106c of the culture vessel, thereby preventing water condensation at the inner peripheral surface of the culture vessel.

Figure 4:
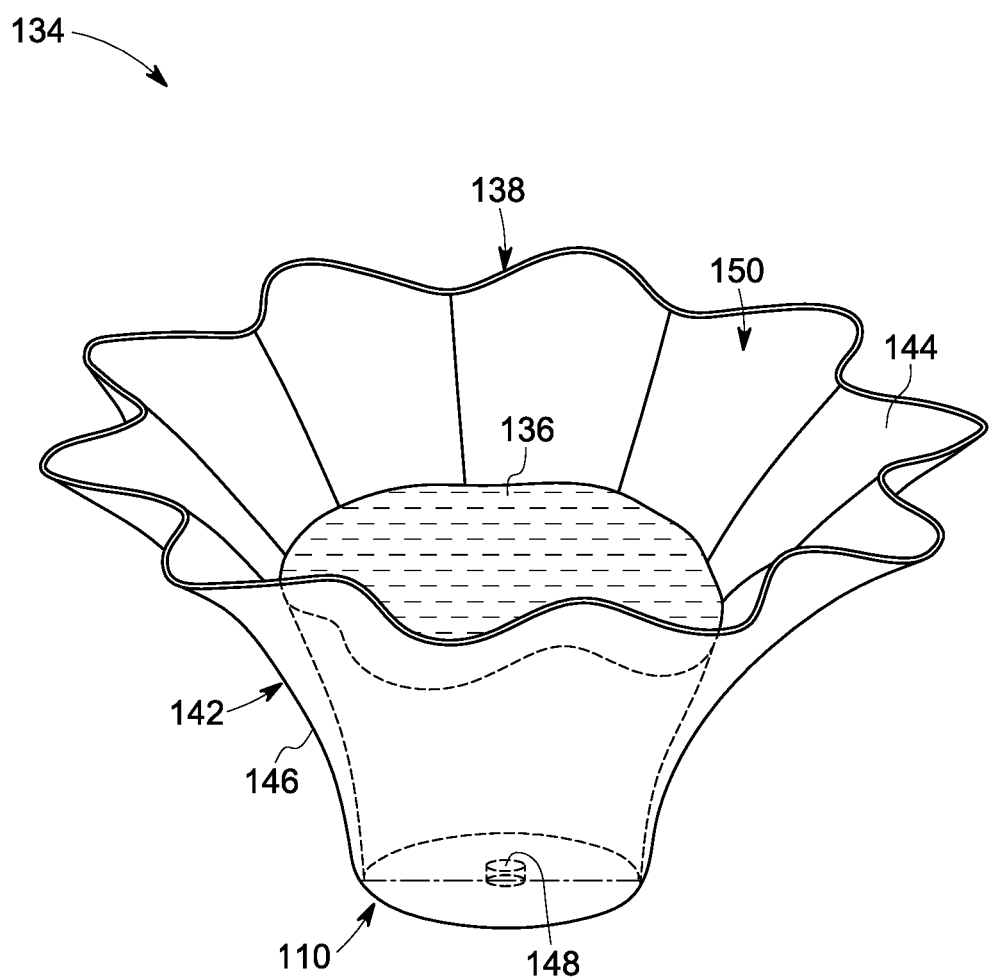
FIG. 4 is a perspective view of a culture vessel of a bioreactor in accordance with one exemplary embodiment.

FIG. 4 illustrates a perspective view of a culture vessel 134 of a bioreactor in accordance with one exemplary embodiment. In the illustrated embodiment, the culture vessel 134 is a disposable container having a flower-shaped structure. The culture vessel 134 is configured to receive a cell-culture media 136 and cultured cells and grow the cultured cells within the culture vessel 134. In certain embodiments, the cell-culture media 136 is transferred to the culture vessel 134 and the plurality of cells are later transferred to the culture vessel 134 using a suitable cells transferring device.

The culture vessel 134 includes a top end portion 138, a bottom end portion 140, a side wall 142 having an inner peripheral surface 144, and an outer peripheral surface 146. The side wall 142 extends between the top end portion 138 and the bottom end portion 140. In the illustrated embodiment, the bottom end portion 140 includes a closed-slot 148 configured to hold one or more temperature sensors (not shown in FIG. 4) for generating input signals representative of temperature of the cell-culture media 136. The culture vessel 134 further includes an opening 150 at the top end portion 138, to receive a heating lid (not shown in FIG. 4) to cover the opening 150 of the culture vessel 134. The outer peripheral surface 146 of the culture vessel 134 conforms to the inner peripheral surface 122 (shown in FIG. 2) of the unitary structure 102. In certain embodiments, the culture vessel 134 has a constant surface area to volume ratio and a constant thermal contact area to volume ratio, which facilitates to maintain the pH, DO level, and temperature for culturing the cells.

Figure 5:
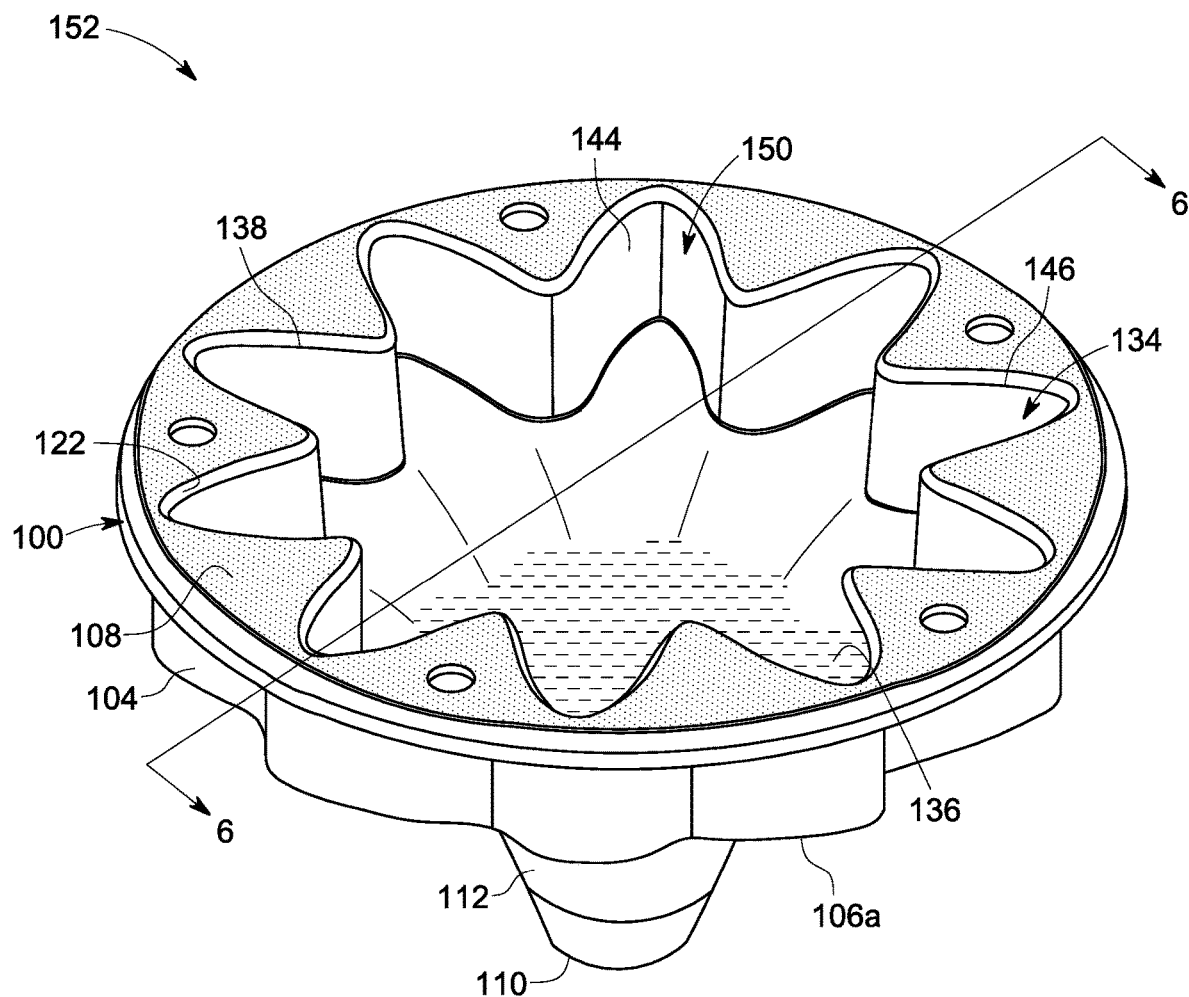
FIG. 5 is a perspective view of a bioreactor in accordance with one exemplary embodiment.

FIG. 5 illustrates a bioreactor 152 in accordance with one exemplary embodiment. The bioreactor 152 includes the heating assembly 100 and the culture vessel 134.

In the illustrated embodiment, the culture vessel 134 is disposed within the cavity 116 (shown in FIG. 2) of the heating assembly 100 such that the outer peripheral surface 146 of the culture vessel 134 is in contact with the inner peripheral surface 122 of the unitary structure 102. The culture vessel 134 is then attached to the unitary structure 102 and filled with cell-culture media 136.

The heating component 104 is coupled to the top segment 106a and configured to heat the culture vessel 134 through the side wall 112 of the unitary structure 102. The heating component 104 is configured to establish temperature gradient along the culture vessel 134 from the top end 108 to the bottom end 110 to prevent water condensation along the side wall of the culture vessel 134. In one non-limiting embodiment, the heating lid (not shown in FIG. 5) disposed at the opening 150 is further configured to heat the culture vessel 134. Such a heating lid may further include a plurality of ports such as inlet ports for supplying cell-culture media 136, nutrient, and gases to the culture vessel 134 and discharge ports for discharging gases from the culture vessel 134. In some embodiments, the heating lid may further include an opening to receive and support an impeller for agitating the cell-culture media 136 filled in the culture vessel 134.

Figure 6:
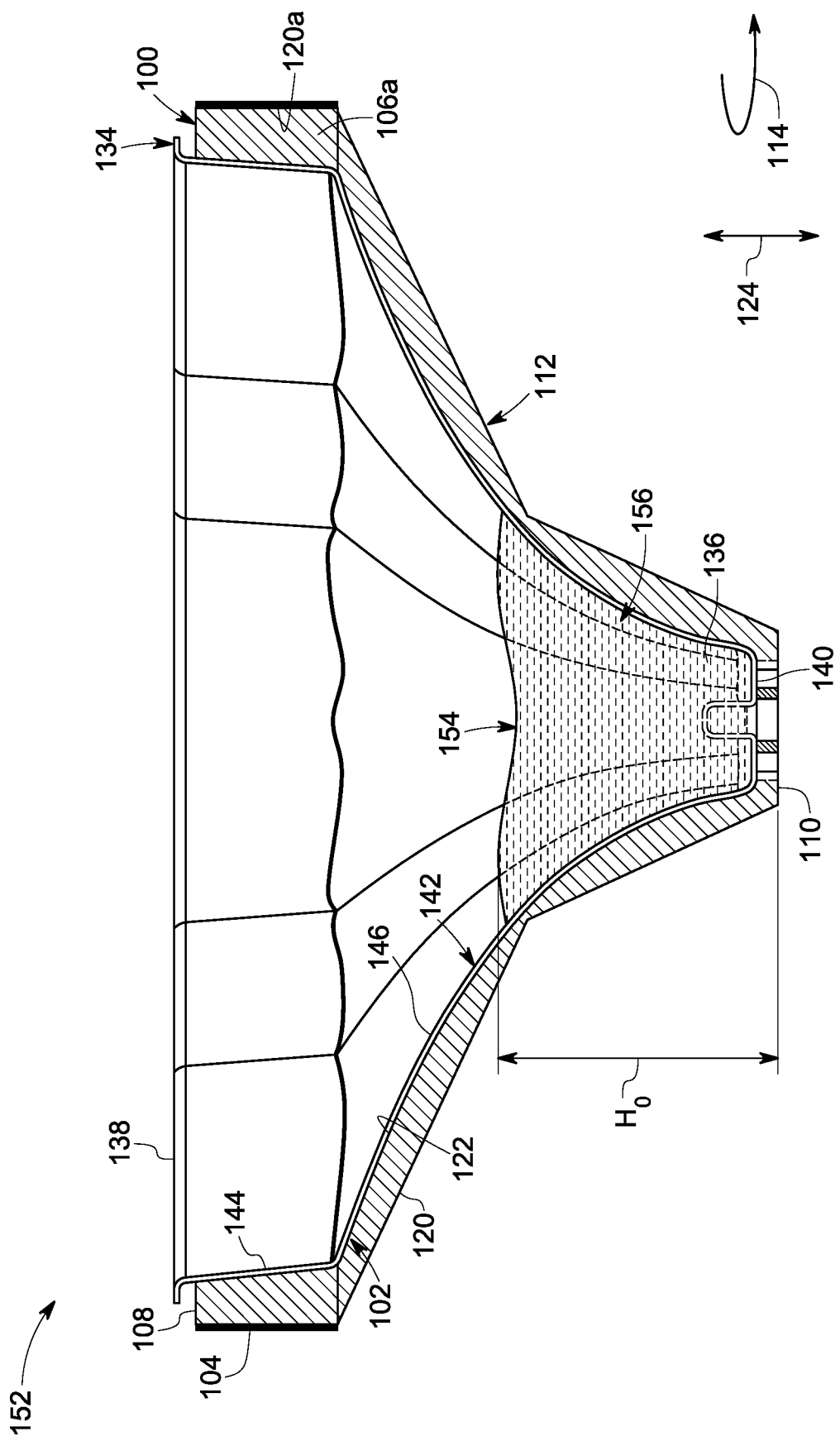
FIG. 6 is a sectional view of the bioreactor taken along line 6-6 in accordance with the exemplary embodiment of FIG. 5.

FIG. 6 illustrates a sectional view of the bioreactor 152 taken along line 6-6 in accordance with the exemplary embodiment of FIG. 5. The culture vessel 134 is disposed within the unitary structure 102 such that the bottom end portion 140 of the culture vessel 134 is in contact with the bottom end 110 of the unitary structure 102 and the side wall 142 of the culture vessel 134 is in contact with the side wall 112 of the unitary structure 102. Specifically, the outer peripheral surface 146 of the culture vessel 134 is in contact with the inner peripheral surface 122 of the unitary structure 102. The heating component 104 is coupled to the outer peripheral surface portion 120a of top segment 106a of the unitary structure 102 and configured to heat the culture vessel 134 via the side wall of the unitary structure 102. The heating component 104 is configured to heat at least one segment 106a including the top end 108 having a uniform perimeter to establish the temperature gradient along an axial direction 124 of the culture vessel 134. In such embodiments, the heating component 104 has a uniform electrical resistance along the circumferential direction 114 of the heating assembly 100. In the illustrated embodiment, the heating component 104 generates heat at the top segment 106a having the uniform perimeter. The heat is conducted to the remaining portion 106b of the unitary structure 102, along the axial direction 124 of the heating assembly 100. As a result, the temperature gradient is established and maintained along the culture vessel 134 of the bioreactor 152.

The culture vessel 134 is designed to accommodate substantial changes in volume of the cell-culture media 136 which does not affect the bioreactor dynamics. It should be noted herein that the term "bioreactor dynamics" refers to how fast a plurality of internal parameters of the bioreactor changes with respect to change in at least one external parameter. In one non-limiting embodiment, the plurality of internal parameters which governs the culturing of cells includes potential of Hydrogen (pH), dissolved oxygen (DO) in the cell-culture media 136, temperature, and mixing/agitating speed. For example, when one of the external parameter such as heating temperature of the culture vessel 134 changes, the temperature of the cell-culture media 136 changes accordingly. Varying one or more internal parameters such as pH, dissolved oxygen (DO) in the cell-culture media 136, and temperature of the cell-culture media 136 adversely affects growth of the cells.

A top surface area of the cell-culture media 136 at height "$H_O$" of the culture vessel 134 is referred to herein as a gas transfer area (GTA) 154. Similarly, a surface area of the culture vessel 134 at height "$H_O$", which is in contact with the cell-culture media 136 during cell culturing, may be referred to herein as a heat transfer area (HTA) 156. A volume of the cell-culture media 136 in the culture vessel 134 is referred to herein as a total volume "V". In one or more embodiments, the inner peripheral surface 144 of the culture vessel 134 facilitates to maintain a constant "GTA" to "V" ratio, which is referred to as a specific gas transfer area ($_SGTA$). The inner peripheral surface 144 of the culture vessel 134 also facilitates to maintain a constant "HTA" to "V" ratio, which is referred to as a specific heat transfer area ($_SHTA$). Such a culture vessel 134 having the $_SGTA$ and $_SHTA$ facilitates to maintain an appropriate pH, dissolved oxygen (DO), and temperature of the cell-culture media 136 for growth of the cells.

Figure 7:
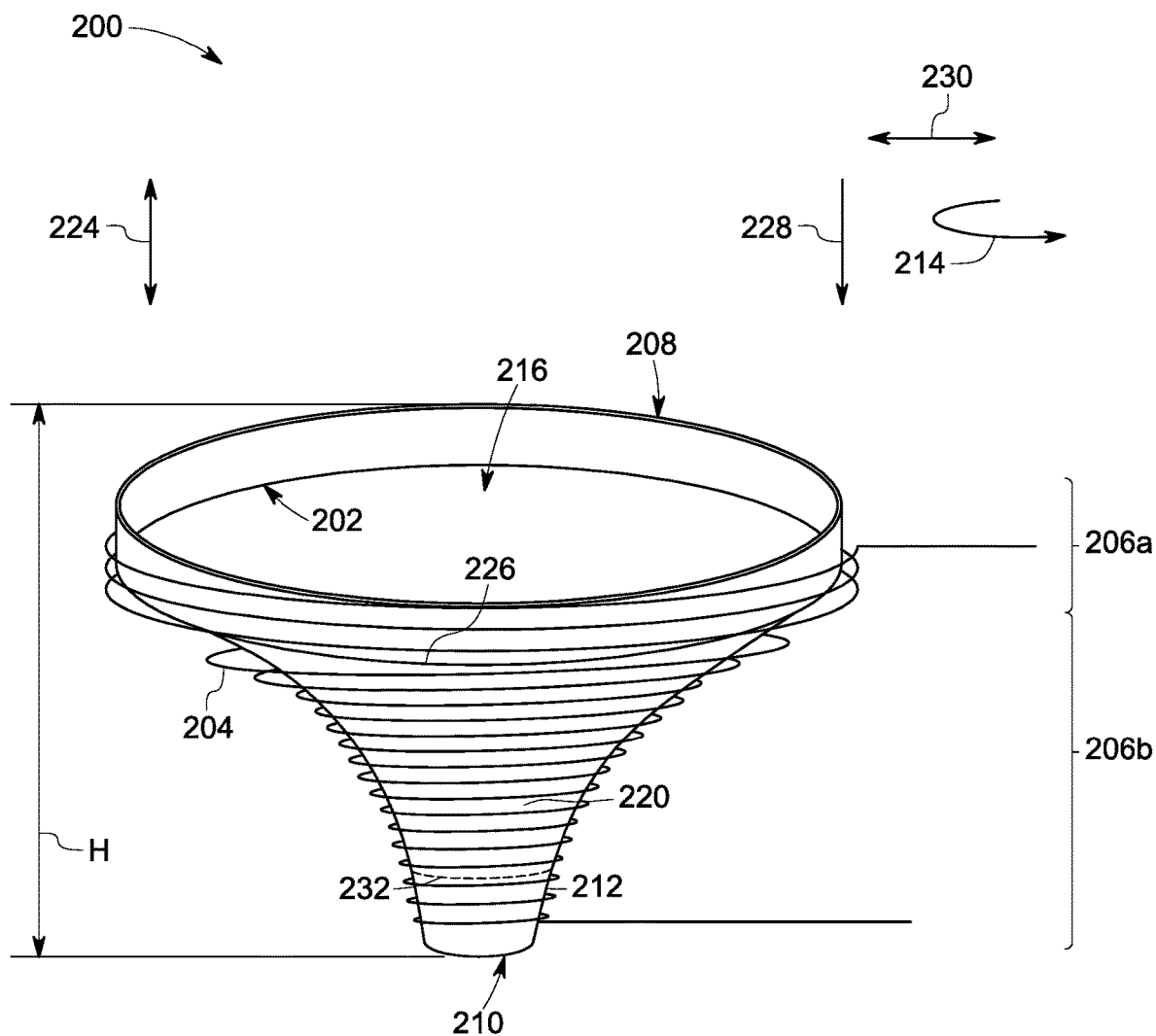
FIG. 7 is a perspective view of a heating assembly in accordance with another exemplary embodiment.

FIG. 7 illustrates a perspective view of a heating assembly 200 in accordance with another exemplary embodiment. The heating assembly 200 includes a holder 202 (also referred to as "a unitary structure") and a heating component 204. The unitary structure 202 has a conical shaped unitary structure. The unitary structure 202 includes a top end 208, a bottom end 210, and a side wall 212 extending between the top end 208 and the bottom end 210 and along a circumferential direction 214 of the heating assembly 200 to define a cavity 216 there between. The holder 202 includes a first segment 206a disposed proximate to the top end 208 and a second segment 206b. The first segment 206a has a uniform perimeter 226 and the second segment 206b has a gradually varied perimeter 232 along a direction 228 perpendicular to a plane 230 which intersects the side wall 212 and is parallel to the top end 208 and the bottom end 210. Specifically, the second segment 206b has a gradually varying perimeter 232 along an axial direction 224 of the heating assembly 200. In one or more embodiments, the gradually varying perimeter 232 facilitates to maintain a constant "GTA" to "V" ratio.

The heating component 204 is disposed spirally around an outer peripheral surface 220 of the side wall 212 from the top end 208 to the bottom end 210. Ends of the heating component 204 are coupled to a power source.

Figure 8:
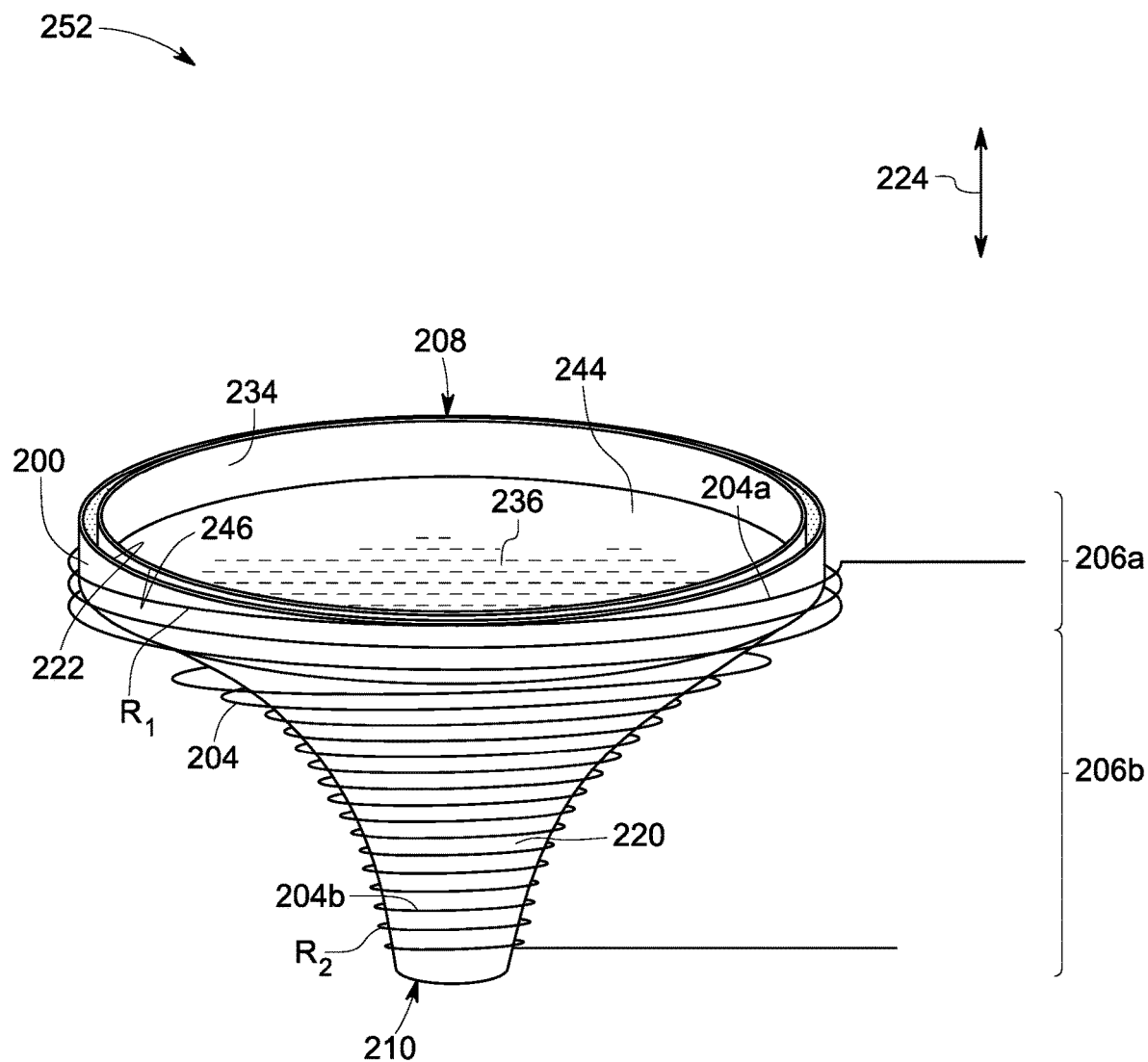
FIG. 8 is a perspective view of a bioreactor in accordance with one exemplary embodiment.

FIG. 8 illustrates a perspective view of a bioreactor 252 in accordance with one exemplary embodiment. The bioreactor 252 includes the heating assembly 200 and a culture vessel 234 disposed within the cavity 216 (shown in FIG. 7) of the heating assembly 200. An inner peripheral surface 222 of the heating assembly 200 is contacted with an outer peripheral surface 246 of the culture vessel 234. In such an embodiment, the inner peripheral surface 222 of the heating assembly 200 is substantially similar to the outer peripheral surface 246 of the culture vessel 234. Further, the heating component 204 has a gradually varied electrical resistance. For example, a first portion 204a of the heating component 204 has a first electrical resistance "$R_1$" and a second portion 204b of the heating component 204 has a second electrical resistance "$R_2$". The first electrical resistance "$R_1$" is different from the second electrical resistance "$R_2$". In the illustrated embodiment, the electrical resistance gradually decreases from the top end 208 to the bottom end 210. In some other embodiments, the electrical resistance may gradually increase from the top end 208 to the bottom end 210.

The culture vessel 234 is used to receive a cell-culture media 236 including a plurality of cells. The heating component 204 is used to heat the cell-culture media 236 to establish and maintain a temperature gradient along the culture vessel 234 from the top end 208 to the bottom end 210, thereby preventing water condensation along an inner peripheral surface 244 of the culture vessel 234. The heating component 204 generates more heat at portions having greater electrical resistance and less heat at portions having smaller electrical resistance. Specifically, the first portion 204a generates more heat and the second portion 204b generates les heat. As a result, the heating component 204 facilitates to establish and maintain temperature gradient along an axial direction 224 of the culture vessel 234 of the bioreactor 252. In the illustrated embodiment, the heating component 204 generates larger amount of heat at the first segment 206a having greater electrical resistance and uniform perimeter and smaller amount of heat at the second segment 206b having the smaller electrical resistance and gradually varied perimeter, along the axial direction 224 of the heating assembly 200. As a result, the temperature gradient is established and maintained along the culture vessel 234 of the bioreactor 252.

Figure 9:
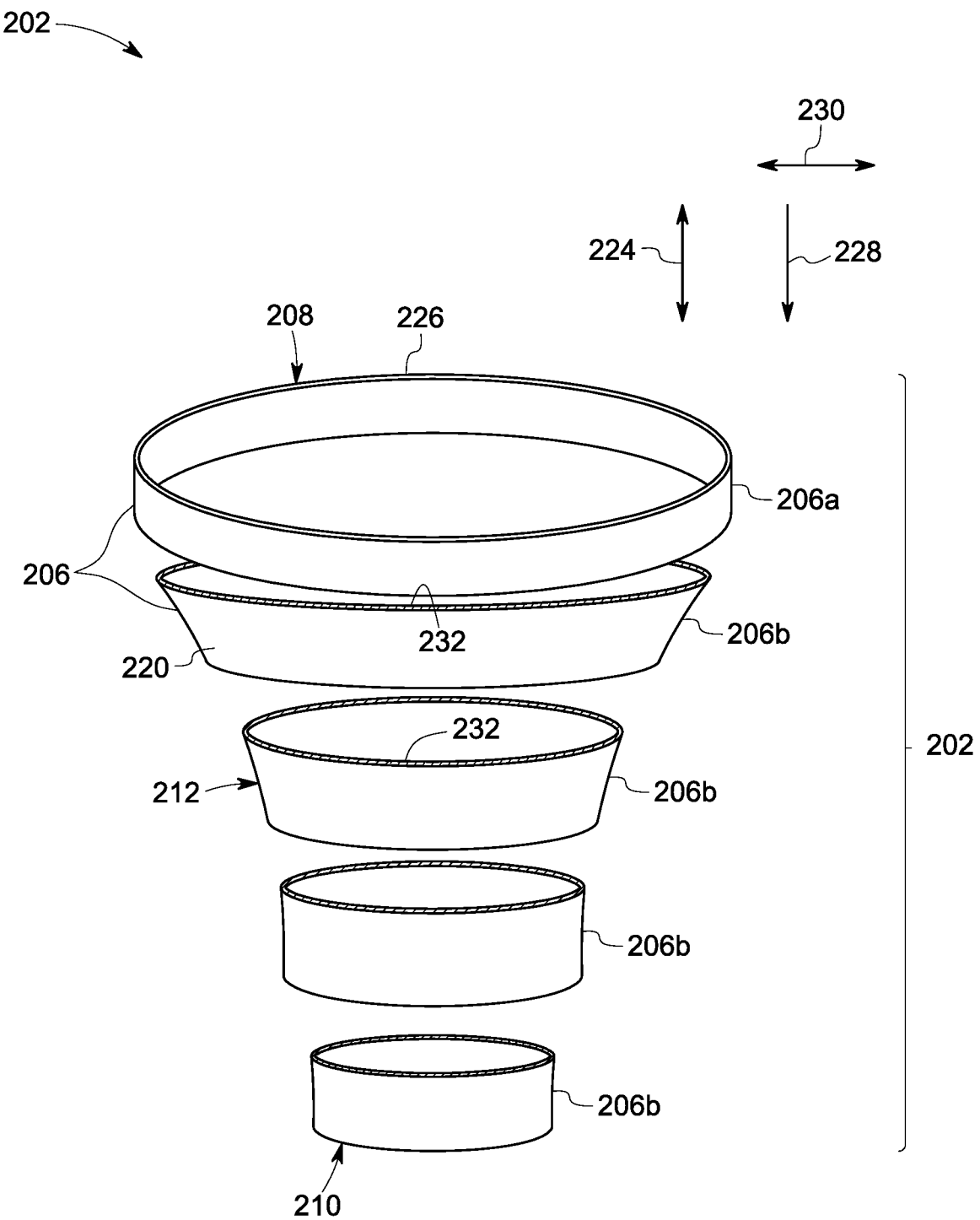
FIG. 9 is an exploded sectional view of a holder of a heating assembly in accordance with one exemplary embodiment.

FIG. 9 illustrates an exploded perspective view of the holder 202 of the heating assembly 200 in accordance with one exemplary embodiment. The holder 202 includes a plurality of segments 206 coupled to each other (as shown in FIGS. 7 and 8) to define a unitary structure. In the illustrated embodiment, the plurality of segments 206 is stacked along an axial direction 224 of the heating assembly 200.

A first segment 206a of the plurality of segments 206, has a uniform perimeter 226 along a direction 228 perpendicular to a plane 230 which intersects the outer peripheral surface 220 of the side wall 212 and is parallel to the top end 208 and the bottom end 210. The first segment 206a is coupled to the top end 208. A plurality of second segment 206b have a gradually varied perimeter 232 along the direction 228 perpendicular to the plane 230 which intersects the outer peripheral surface 220 of the side wall 212 and is parallel to the top end 208 and the bottom end 210.

Figure 10:
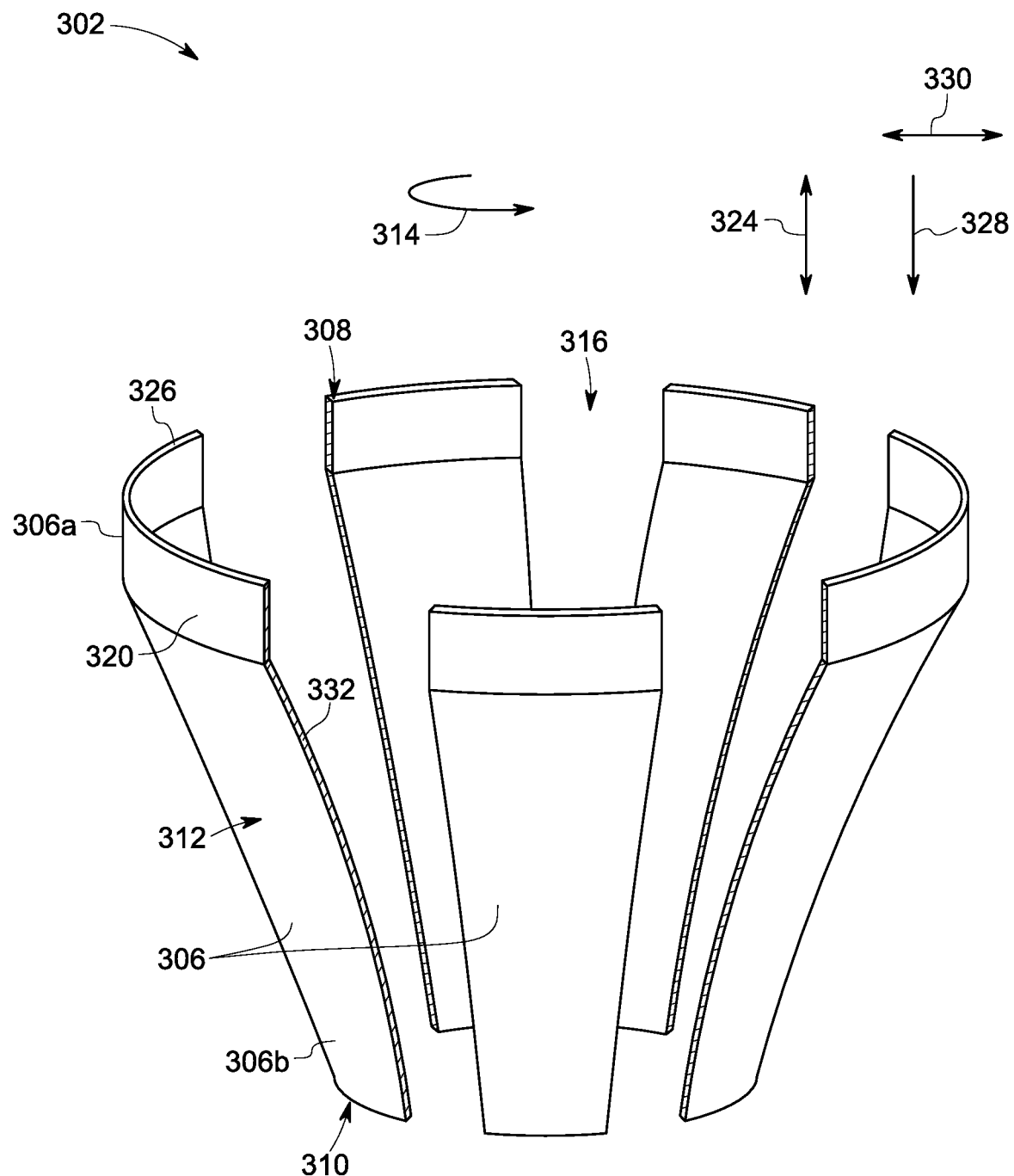
FIG. 10 is an exploded perspective view of a holder of a heating assembly in accordance with another exemplary embodiment.

FIG. 10 illustrates an exploded sectional view of a holder 302 of a heating assembly in accordance with another exemplary embodiment. The holder 302 (also referred to as "a unitary structure") includes a plurality of segments 306 coupled to each other to define a unitary structure. In the illustrated embodiment, the plurality of segments 306 is disposed adjacent to each other along a circumferential direction 314 of the heating assembly to define a cavity 316 there between.

The unitary structure 302 has a portion 306a having a uniform perimeter 326 along a direction 328 perpendicular to a plane 330 which intersects an outer peripheral surface 320 of a side wall 312 and is parallel to a top end 308 and a bottom end 310. The unitary structure 302 further includes another portion 306b having a gradually varied perimeter 332 along the direction 328 perpendicular to the plane 330 which intersects the outer peripheral surface 320 of the side wall 312 and is parallel to the top end 308 and the bottom end 310.

Figure 11:
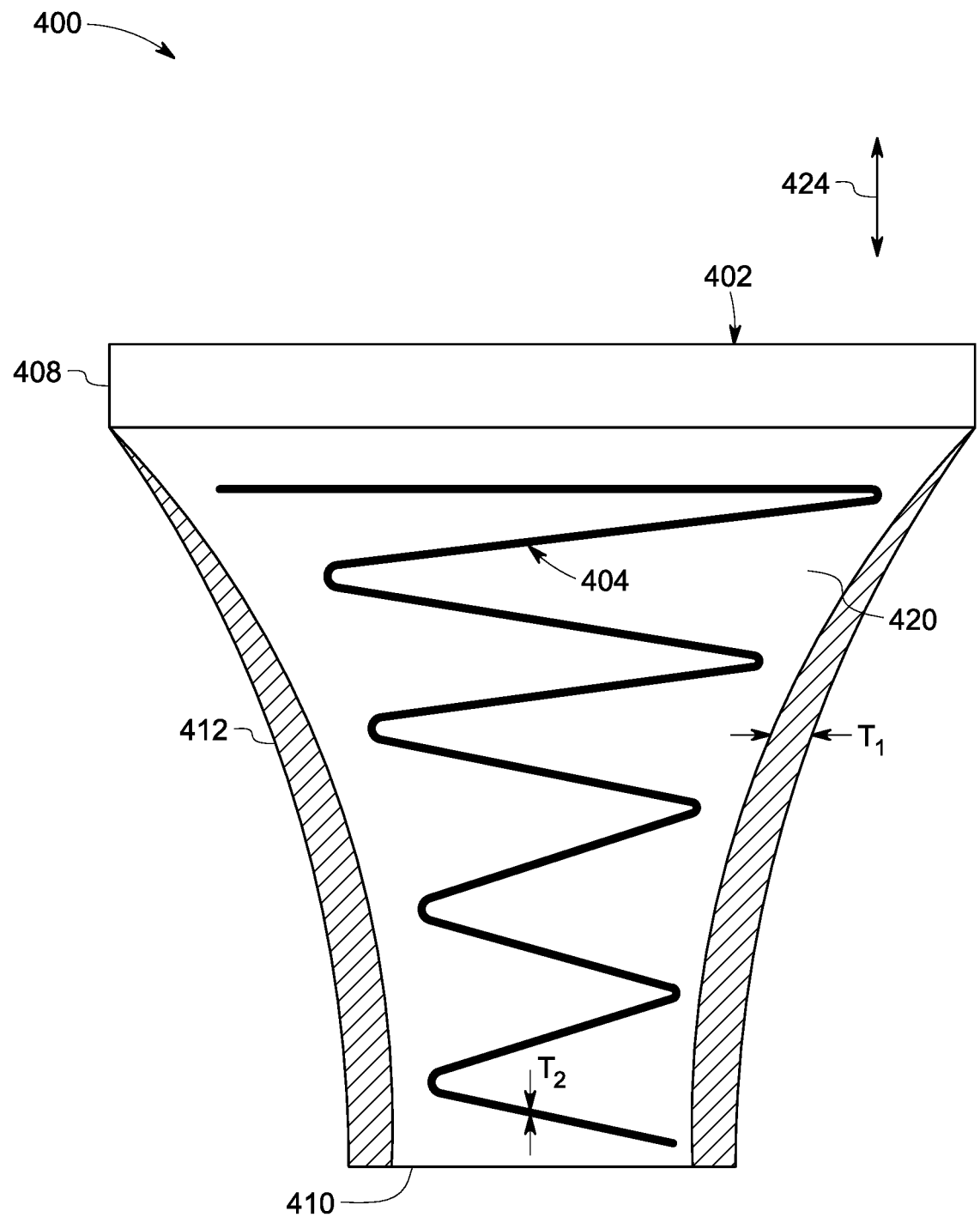
FIG. 11 is a schematic diagram of a heating assembly including a holder having a side wall with a gradually varied thickness and a heating component in accordance with one exemplary embodiment.

FIG. 11 illustrates a schematic diagram of a heating assembly 400 in accordance with another exemplary embodiment. The heating assembly 400 includes a holder 402 (also referred to as "a unitary structure") and a heating component 404.

The holder 402 includes a plurality of segments coupled to each other to define a unitary structure. The unitary structure 402 includes a top end 408, a bottom end 410, and a side wall 412 extending between the top end 408 and the bottom end 410. In the illustrated embodiment, the side wall 412 has a gradually varied thickness "$T_1$" from the top end 408 to the bottom end 410. The heating component 404 is disposed on an outer peripheral surface 420 of the unitary structure 402 and extends along an axial direction 424 of the heating assembly 400. Specifically, the heating component 404 has a wave-like structure. The heating component 404 is disposed on the outer peripheral surface 420, extending from the top end 408 to the bottom end 410. Further, the heating component 404 has a uniform thickness "$T_2$" from the top end 408 to the bottom end 410. Further, the heating component 404 has a uniform electrical resistance along the axial direction 424 of the heating assembly 400. In the illustrated embodiment, the thickness "$T_1$" gradually increases from the top end 408 to the bottom end 410. In some other embodiments, the thickness "$T_1$" may gradually decrease from the top end 408 to the bottom end 410.

A surface area at the top end 408 of the unitary structure 402 is substantially greater than a surface area at the bottom end 410 of the unitary structure 402. Hence, the heat required to heat the top end 408 is substantially greater compared to heat required to heat the bottom end 410. The heating component 404 generates more heat at portions having smaller thickness and less heat at portions having greater thickness. As a result, the gradually varied thickness "$T_1$" of the side wall 412 and uniform thickness "$T_2$" of the heating component 404 facilitates to establish and maintain temperature gradient along a culture vessel of a bioreactor (not shown in FIG. 11).

Figure 12:
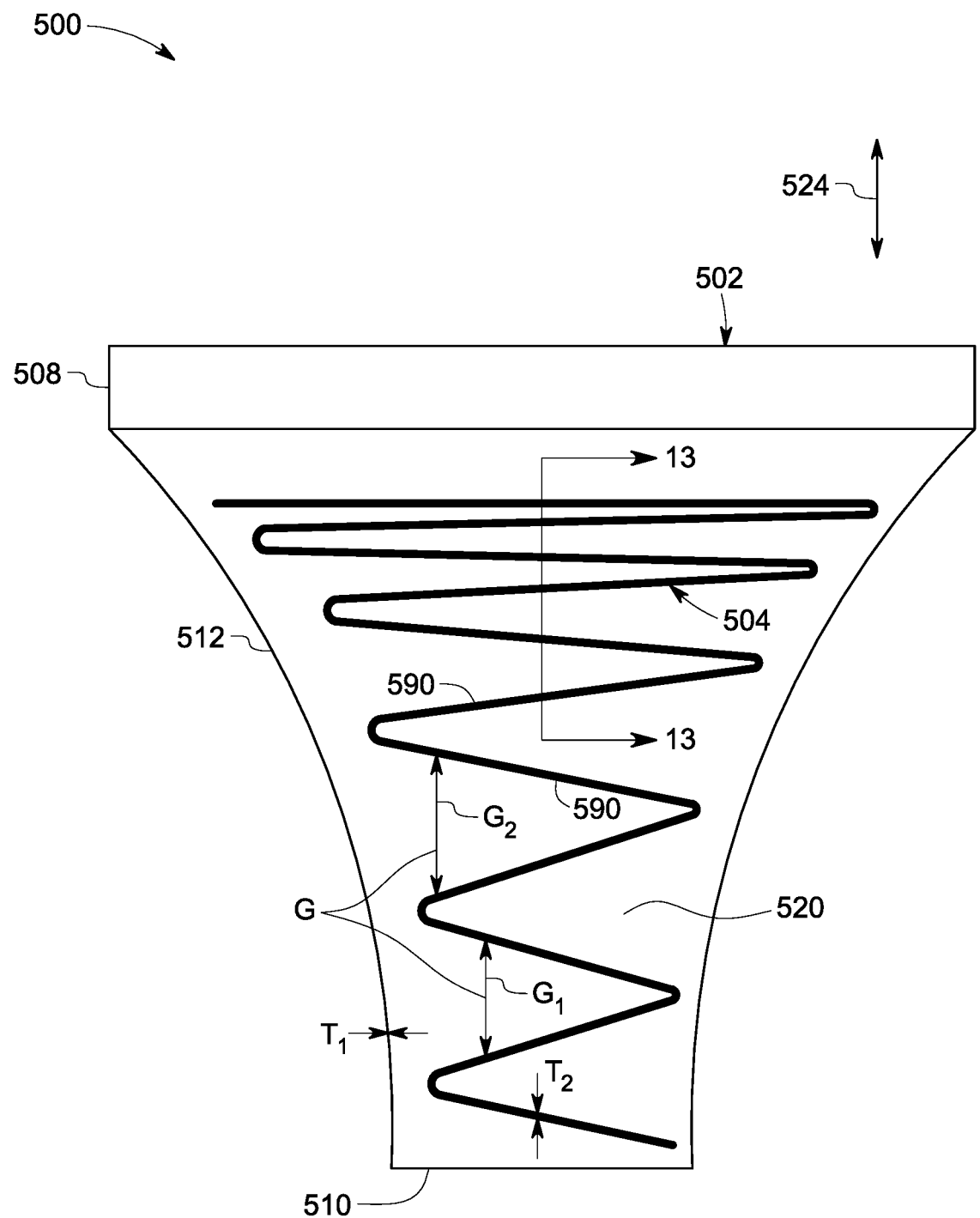
FIG. 12 is a schematic diagram of a heating assembly including a holder and a heating component having a wave-like structure in accordance with one exemplary embodiment.

FIG. 12 illustrates a schematic diagram of a heating assembly 500 in accordance with another exemplary embodiment. The heating assembly 500 includes a holder 502 (also referred to as "a unitary structure") and a heating component 504.

The holder 502 includes a plurality of segments coupled to each other to define a unitary structure. The unitary structure 502 includes a top end 508, a bottom end 510, and a side wall 512 extending between the top end 508 and the bottom end 510. In the illustrated embodiment, the side wall 512 has a uniform thickness "$T_1$" from the top end 508 to the bottom end 510. The heating component 404 has a wave-like structure disposed on an outer peripheral surface 520 of the unitary structure 502. The heating component 504 extends along an axial direction 524 of the heating assembly 500. The heating component 504 has a gradually varied thickness "$T_2$" from the top end 508 to the bottom end 510. Further, the heating component 504 has a uniform electrical resistance along the axial direction 524 of the heating assembly 500. The heating component 504 has a plurality of turns 590 separated from each other by a gap to form a plurality of gradually varied gaps "G" from the top end 508 to the bottom end 510. In certain embodiments, the plurality of gradually varied gaps "G" may be referred to as a "wave length" in a spatial domain. For example, a first gap "$G_1$" is different from a second gap "$G_2$". In the illustrated embodiment, the plurality of gradually varied gaps "G" gradually increases from the top end 508 to the bottom end 510. In some other embodiments, the plurality of gradually varied gaps "G" may gradually decrease from the top end 508 to the bottom end 510. In certain embodiments, the plurality of gradually varied gaps "G" of the heating component 504 varies an amount of heat output supplied by the heating component 504 along an axial direction 524 of the heating assembly 500, thereby facilitates to establish and maintain a temperature gradient along a culture vessel of a bioreactor (not shown in FIG. 12). In the illustrated embodiment, heating component 504 generates smaller amount of heat at portions having smaller gaps and larger amount of heat at portions having larger gaps, along the axial direction 524 of the heating assembly 500. As the result, the temperature gradient is established and maintained along the culture vessel of the bioreactor.

Figure 13:
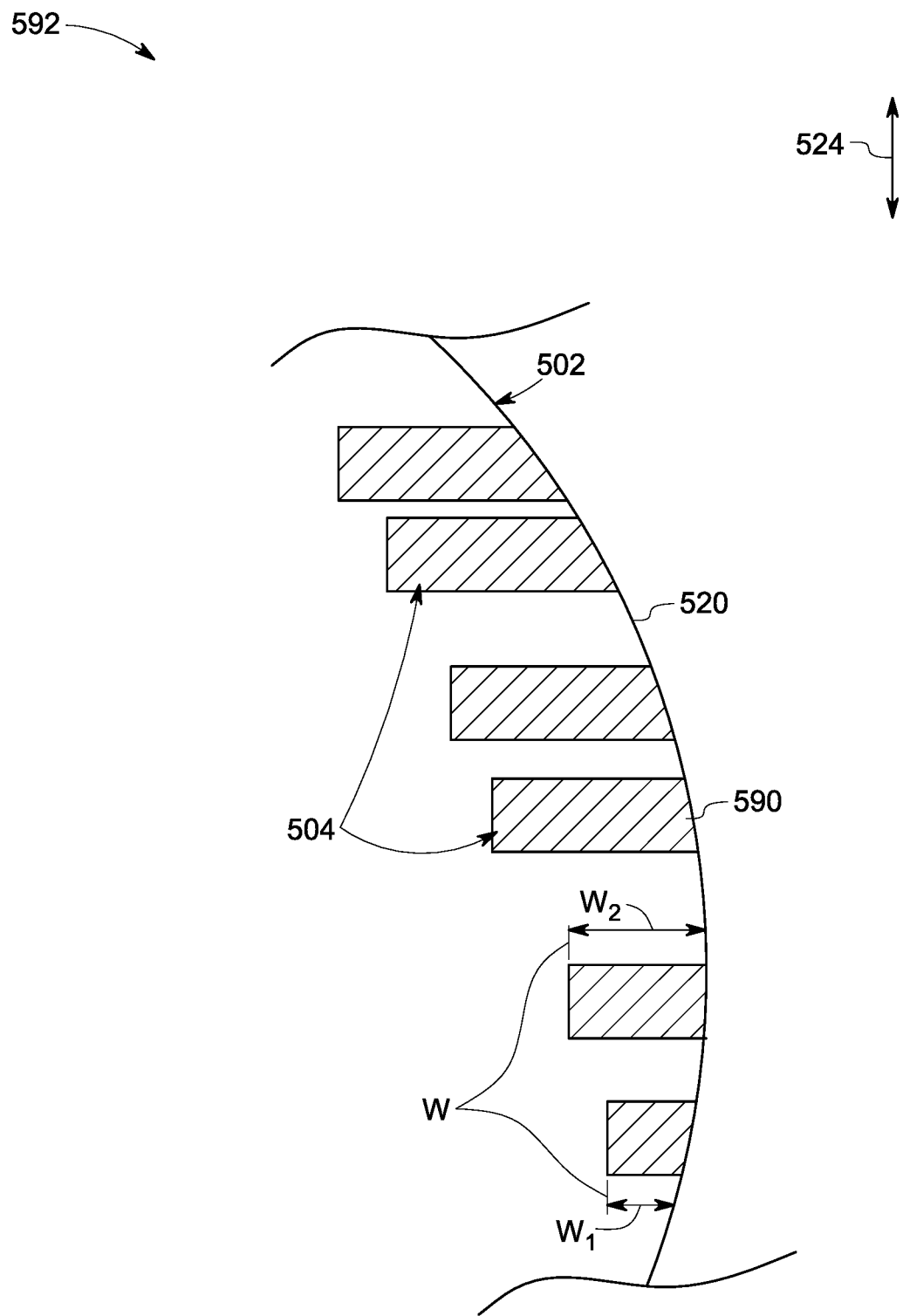
FIG. 13 is a sectional view of a portion of the heating assembly taken along line 13-13 in accordance with the exemplary embodiment of FIG. 12.

FIG. 13 illustrates a sectional view of a portion 592 of the heating assembly 500 taken along line 13-13 in accordance with the exemplary embodiment of FIG. 12. In the illustrated embodiment, heating component 504 has a gradually varied width "W" from the top end 508 to the bottom end 510. For example, a first width "$W_1$" is different from a second width "$W_2$". In the illustrated embodiment, the gradually varied width "W" gradually decreases from the top end 508 to the bottom end 510. In some other embodiments, the gradually varied width "W" may gradually increase from the top end 508 to the bottom end 510. The gradually varied width "W" of the heating component 504 varies an amount of heat output supplied by the heating component 504 along an axial direction 524 of the heating assembly 500, thereby facilitates to establish and maintain a temperature gradient along the culture vessel of the bioreactor. In the illustrated embodiment, the heating component 504 generates larger amount of heat at portions having smaller width and smaller amount of heat at portions having larger width, along the axial direction 524 of the heating assembly 500. As a result, the temperature gradient is established and maintained along the culture vessel of the bioreactor.

Figure 14:
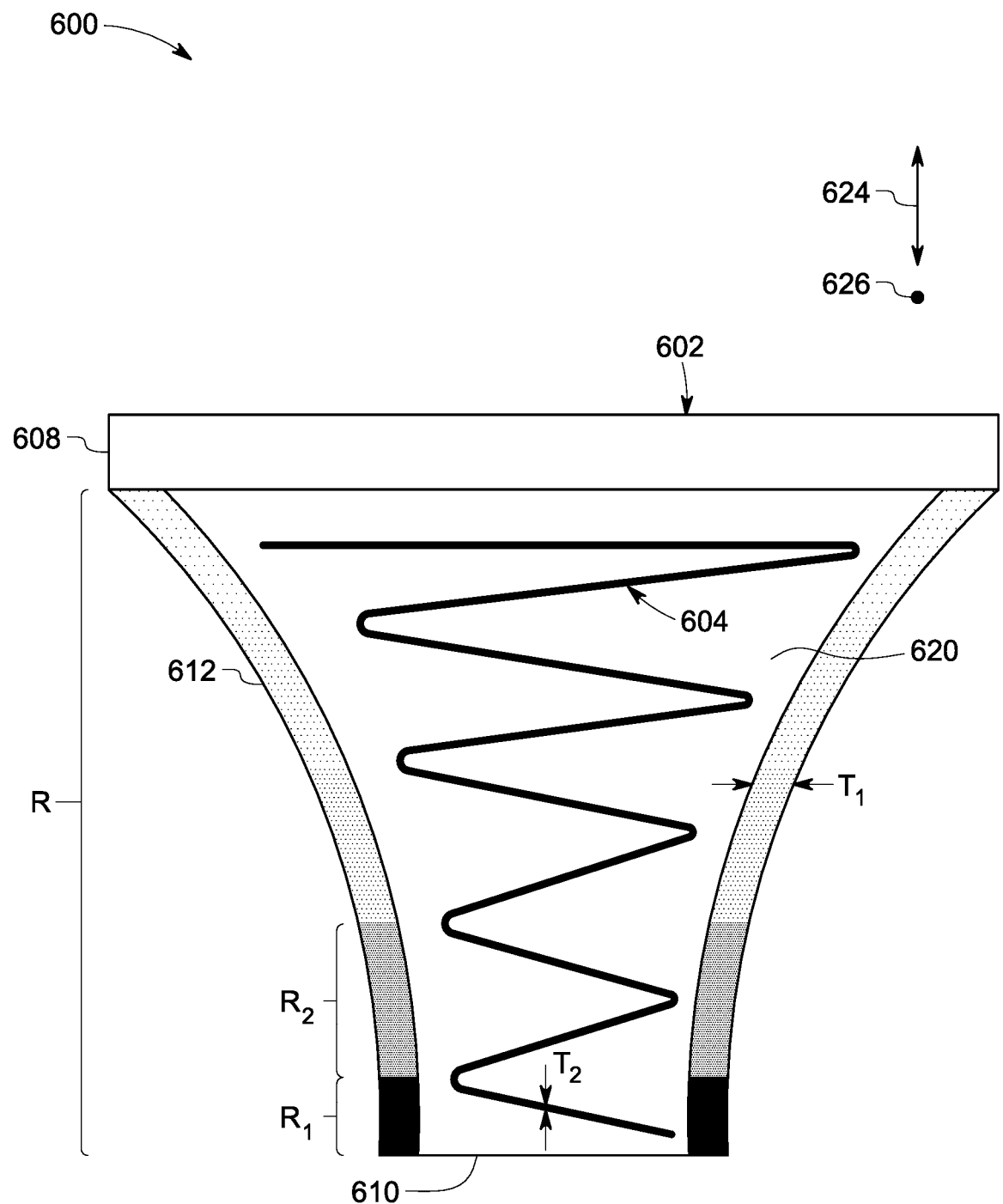
FIG. 14 is a schematic diagram of a heating assembly including a holder having a side wall with a gradually varied thermal resistance in accordance with one exemplary embodiment.

FIG. 14 illustrates a schematic diagram of a heating assembly 600 in accordance with another exemplary embodiment. The heating assembly 600 includes a holder 602 (also referred to as "a unitary structure") and a heating component 604.

The holder 602 includes a plurality of segments coupled to each other to define a unitary structure. The unitary structure 602 includes a top end 608, a bottom end 610, and a side wall 612 extending between the top end 608 and the bottom end 610. In the illustrated embodiment, the side wall 612 has a uniform thickness "$T_1$" from the top end 608 to the bottom end 610. The heating component 604 has a wave-like structure disposed on an outer peripheral surface 620 from the top end 608 to the bottom end 610. The heating component 604 has a uniform thickness "$T_2$" from the top end 608 to the bottom end 610. Further, the heating component 604 has a uniform electrical resistance along an axial direction 624 of the heating assembly 600. The side wall 612 has a gradually varied thermal resistance "R" from the top end 608 to the bottom end 610. Specifically, a first thermal resistance "$R_1$" is different from a second thermal resistance "$R_2$". The heat generated by the heating component 604 is conducted along a radial direction 626 of the side wall 612. The side wall 612 is made of different materials having varied thermal resistance "R". In one embodiment, the side wall 612 may have the top end 608 made of a first material and the bottom end 610 made of a second material. In such embodiments, the thermal resistance "R" of the first material may be different from the thermal resistance of the second material. In the illustrated embodiment, the thermal resistance "R" gradually increases from the top end 608 to the bottom end 610. In some other embodiments, the thermal resistance "R" gradually decreases from the top end 608 to the bottom end 610. In certain embodiments, the gradually varied thermal resistance "R" of the side wall 612 results in varied heat conductivity of the unitary structure 602 along the axial direction 624 of the heating assembly 600, thereby facilitates to maintain temperature gradient along a culture vessel of a bioreactor (not shown in FIG. 14). If the thermal resistance of the side wall 612 is greater, the heat conductivity is decreased, resulting in less heating. If the thermal resistance of the side wall 612 is less, the heat conductivity is increased resulting in greater heating. Such a variation in the thermal resistance "R" of the side wall 612 facilities to establish and maintain the temperature gradient along the axial direction 624 of the culture vessel of the bioreactor.

Figure 15:
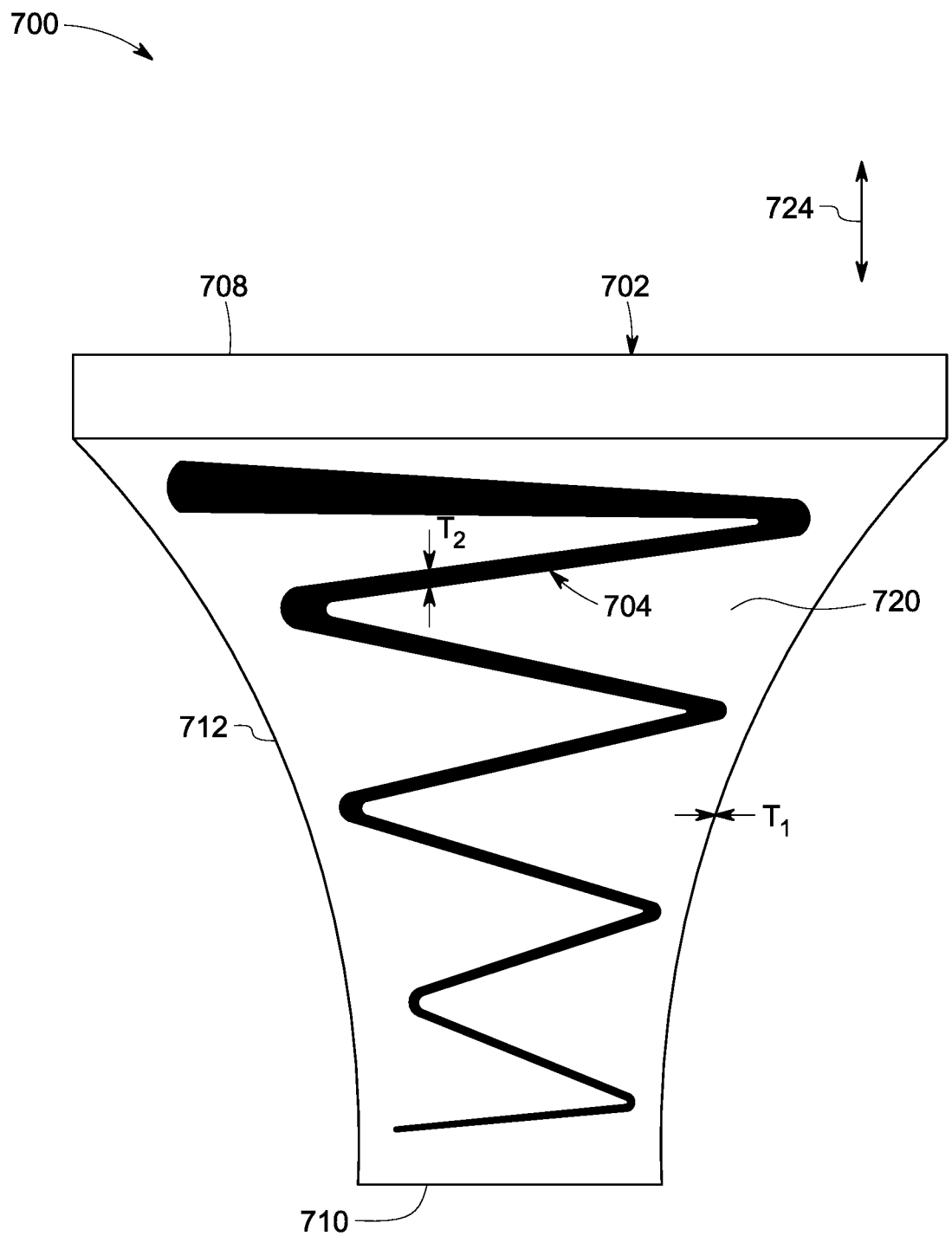
FIG. 15 is a schematic diagram of a heating assembly including a holder and a heating component having a wave-like structure with a gradually varied thickness in accordance with one exemplary embodiment.

FIG. 15 is a schematic diagram of a heating assembly 700 in accordance with one exemplary embodiment. The heating assembly 700 includes a holder 702 and a heating component 704.

The holder 702 includes a plurality of segments coupled to each other to define a unitary structure. The unitary structure 702 includes a top end 708, a bottom end 710, and a side wall 712 extending between the top end 708 and the bottom end 710. In the illustrated embodiment, the side wall 712 has a uniform thickness "$T_1$" from the top end 708 to the bottom end 710. The heating component 704 is disposed on an outer peripheral surface 720 of the unitary structure 702 and extends along an axial direction 724 of the heating assembly 700. Specifically, the heating component 704 has a wave-like structure having a uniform electrical resistance along the axial direction 724 of the heating assembly 700. Further, the heating component 704 has a gradually varied thickness "$T_2$" from the top end 708 to the bottom end 710. In the illustrated embodiment, the thickness "$T_2$" gradually decreases from the top end 708 to the bottom end 710. In some other embodiments, the thickness "$T_2$" may gradually increase from the top end 708 to the bottom end 710.

A surface area of the top end 708 is substantially greater than a surface area of the bottom end 710 of the unitary structure 702. Hence, the heat required to heat the top end 708 is substantially greater compared to heat required to heat the bottom end 710. The heating component 704 generates less heat at portions having greater thickness and more heat at portions having smaller thickness. As a result, the uniform thickness "$T_1$" of the side wall 712 and gradually varied thickness "$T_2$" of the heating component 704 facilitates to establish and maintain temperature gradient along a culture vessel of a bioreactor (not shown in FIG. 15).

Figure 16:
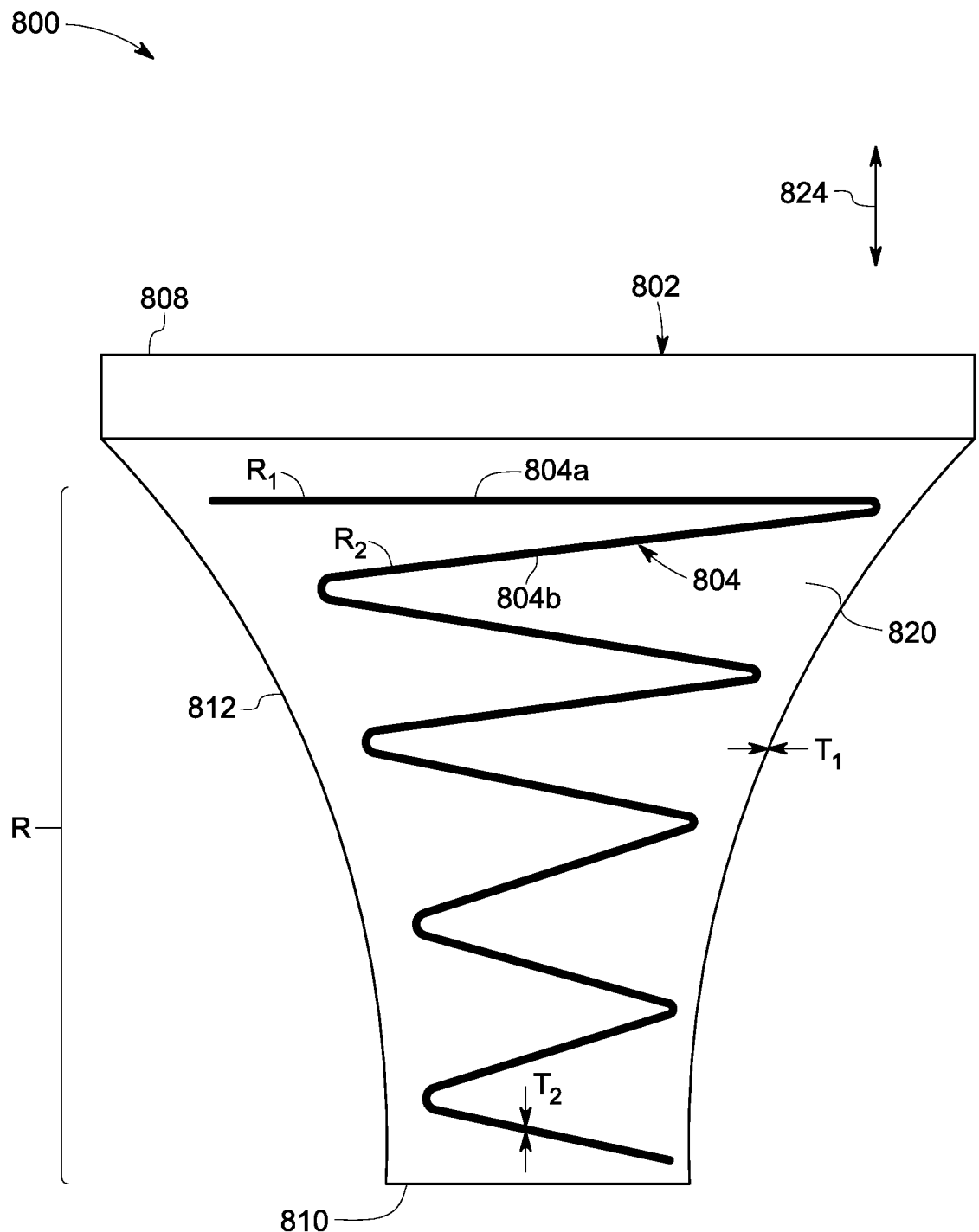
FIG. 16 is a schematic diagram of a heating assembly including a holder and a heating component having a wave-like structure with a gradually varied electrical resistance in accordance with one exemplary embodiment.

FIG. 16 is a schematic diagram of a heating assembly 800 in accordance with one exemplary embodiment. The heating assembly 800 includes a holder 802 and a heating component 804.

The holder 802 includes a plurality of segments coupled to each other to define a unitary structure. The unitary structure 802 includes a top end 808, a bottom end 810, and a side wall 812 extending between the top end 808 and the bottom end 810. In the illustrated embodiment, the side wall 812 has a uniform thickness "$T_1$" from the top end 808 to the bottom end 810. The heating component 804 is disposed on an outer peripheral surface 820 of the unitary structure 802 and extends along an axial direction 824 of the heating assembly 800. Specifically, the heating component 804 has a wave-like structure. Further, the heating component 804 has a uniform thickness "$T_2$" from the top end 808 to the bottom end 810. Additionally, the heating component 804 has a gradually varied electrical resistance "R" from the top end 808 to the bottom end 810. For example, a first portion 804a of the heating component 804 has a first electrical resistance "$R_1$" and a second portion 804b of the heating component 804 has a second electrical resistance "$R_2$". The first electrical resistance "$R_1$" is different from the second electrical resistance "$R_2$". In the illustrated embodiment, the electrical resistance "R" gradually decreases from the top end 808 to the bottom end 810. In some other embodiments, the electrical resistance "R" may gradually increase from the top end 808 to the bottom end 810.

The heating component 804 generates more heat at portions having greater electrical resistance and less heat at portions having smaller electrical resistance. Specifically, the first portion 804a generates more heat and the second portion 804b generates less heat. The uniform thickness "$T_1$" of the side wall 812, the uniform thickness "$T_2$" of the heating component 804, and the gradually varied electrical resistance "R" of the heating component 804 facilitates to establish and maintain temperature gradient along a culture vessel of a bioreactor (not shown in FIG. 16).

Figure 17:
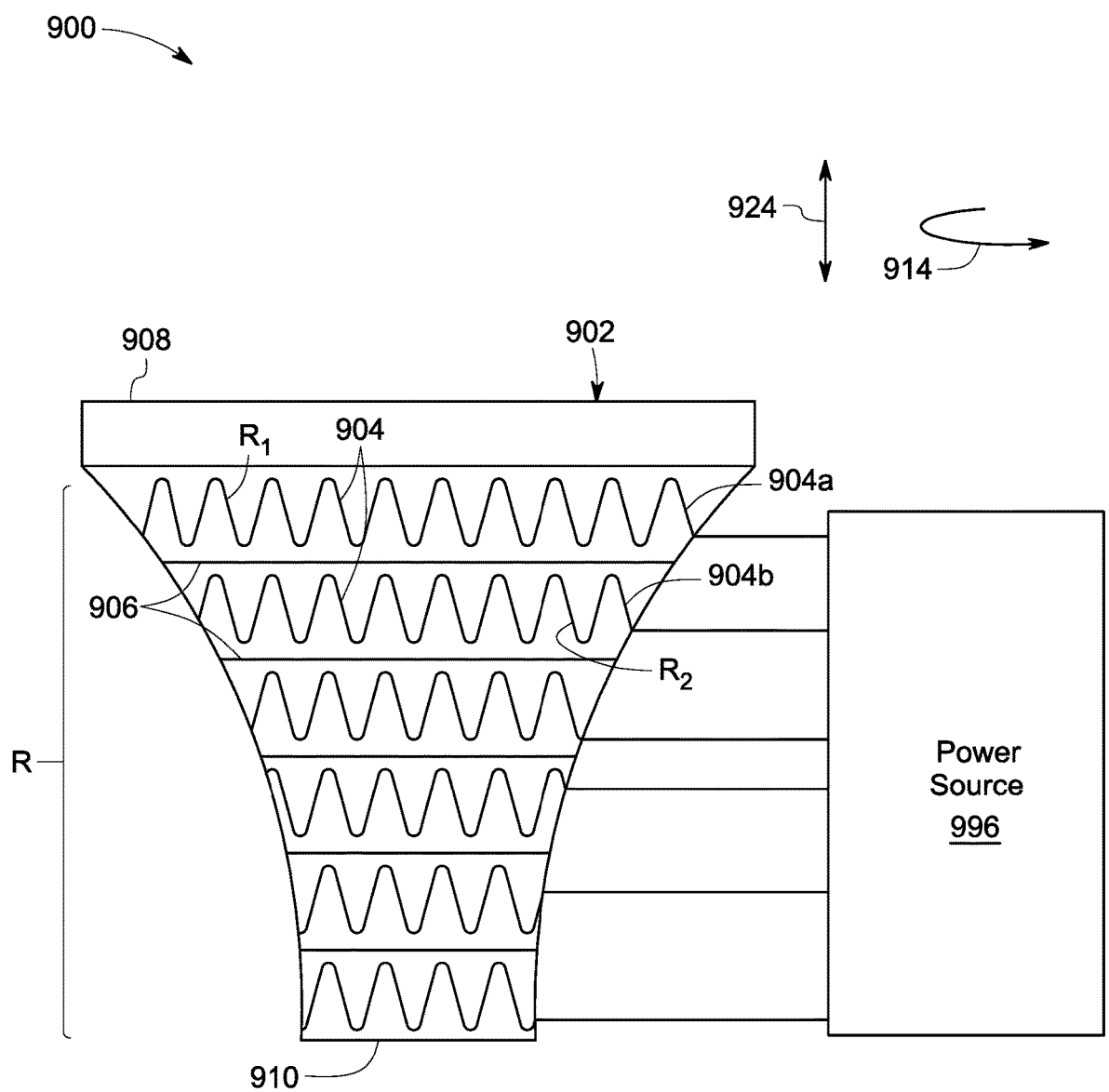
FIG. 17 is a schematic diagram of a heating assembly having a plurality of heating components and a power source in accordance with one exemplary embodiment.

FIG. 17 is a schematic diagram of a heating assembly 900 in accordance with another exemplary embodiment. The heating assembly 900 includes a holder 902 and a plurality of heating components 904.

The holder 902 includes a plurality of segments 906 coupled to each other to define a unitary structure. Specifically, the plurality of segments 906 is stacked along an axial direction 924 of the heating assembly 900. In the illustrated embodiment, the holder 902 has a conical shaped structure. Each of the plurality of heating components 904 is disposed on a corresponding segment of the plurality of segments 906 and extends along a circumferential direction 914 of the heating assembly 900. The plurality of heating components 904 has a gradually varied electrical resistance "R" along the axial direction 924 of the heating assembly 900. For example, a first heating component 904a of the plurality of heating components 904 has a first electrical resistance "$R_1$" and a second heating component 904b of the plurality of heating components 904 has a second electrical resistance "$R_2$". The first electrical resistance "$R_1$" is different from the second electrical resistance "$R_2$". In the illustrated embodiment, the electrical resistance "R" gradually decreases from a top end 908 to a bottom end 910 of the holder 902. In some other embodiments, the electrical resistance "R" may gradually increase from the top end 808 to the bottom end 810. Further, each of the plurality of heating components 904 is coupled to a power source 996. The power source 996 is configured to supply power to each of the plurality of heating components 904 to vary an amount of heat output by each of the plurality of heating components 904 along the axial direction 924 of the heating assembly 900. Specifically, the electrical resistance of each of the heating components 904 varies the heat output by the heating component 904. Such a variation in the electrical resistance in each of the plurality of heating components 904 facilitates to establish and maintain a temperature gradient along a culture vessel of a bioreactor (not shown in FIG. 17).

In some other embodiments, each heating component 904 may extend along the axial direction 924 of the heating assembly 900. In such embodiments, the plurality of segments 906 may be disposed adjacent to each other along the circumferential direction 914 of the heating assembly 900.

Figure 18:
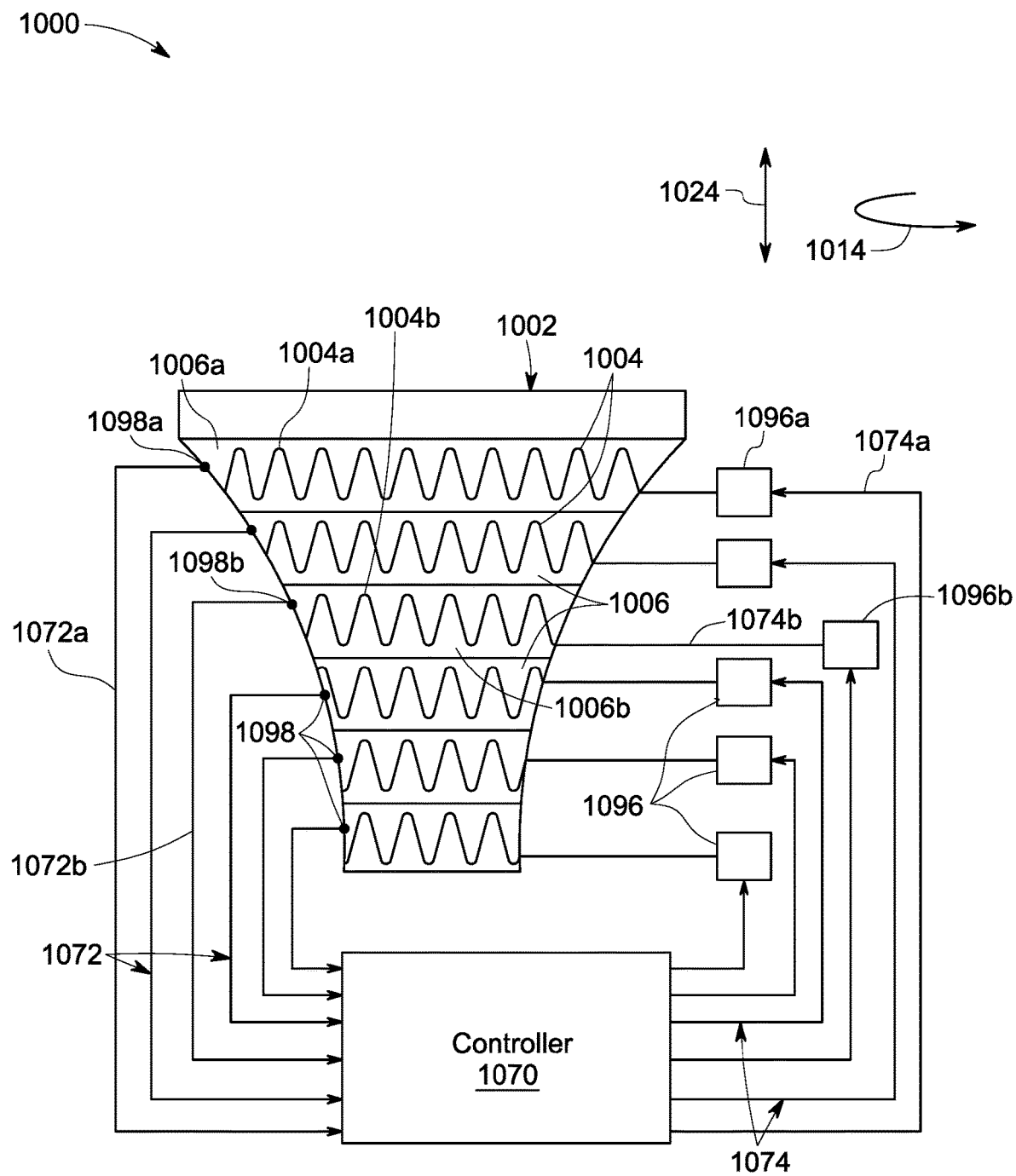
FIG. 18 is a schematic diagram of a heating assembly having a plurality of power sources and a plurality of heating components connected to the corresponding plurality of power sources in accordance with another exemplary embodiment.

FIG. 18 is a schematic diagram of a heating assembly 1000 in accordance with another exemplary embodiment. The heating assembly 1000 includes a holder 1002, a plurality of heating components 1004, a plurality of power sources 1096, a plurality of temperature sensors 1098, and a controller 1070.

The holder 1002 includes a plurality of segments 1006 coupled to each other to define a unitary structure. Specifically, the plurality of segments 1006 is stacked along an axial direction 1024 of the heating assembly 1000. In the illustrated embodiment, the holder 1002 has a conical shaped structure. Each of the plurality of heating components 1004 is disposed on a corresponding segment of a plurality of segments 1006 and extends along a circumferential direction 1014 of the heating assembly 1000. In the illustrated embodiment, each heating component 1004 is coupled to a corresponding power source 1096. Further, each of the plurality of temperature sensors 1098 is coupled to the corresponding segment 1006. The controller 1070 is communicatively coupled to the plurality of temperature sensors 1098 and the plurality of power sources 1096. In one or more embodiments, each of the plurality of temperature sensors 1098 is installed on a portion of the holder 1002 where there is no heating component 1004. Further, each of the temperature sensors 1098 is provided with a thermal insulation member to protect the sensors 1098 from external environment conditions.

In one embodiment, each of the plurality of power sources 1096 is configured to supply power to the corresponding heating component 1004 to generate heat and thereby establish and maintain temperature gradient along a culture vessel of a bioreactor (not shown in FIG. 18). Specifically, one power source 1096a is configured to supply a first power and another power source 1096b is configured to supply a second power different from the first power so as to variably heat each segment 1006 and thereby establish and maintain the temperature gradient along the culture vessel of the bioreactor. In such embodiments, each of the plurality of heating components 1004 has a uniform electrical resistance along the circumferential direction 1014 of the heating assembly 1000.

Each temperature sensor 1098 is configured to generate an input signal 1072 which is representative of temperature of the corresponding segment 1006. The controller 1070 is configured to receive the input signal 1072 from the corresponding temperature sensor 1098 and compare the input signal 1072 with a reference signal to determine whether to vary the power supplied to the corresponding heating component 1004 of the corresponding segment 1006. The controller 1070 is configured to generate a control signal 1076 to regulate the corresponding power source 1096 either by increasing, decreasing, or maintaining the power supplied to the corresponding heating component 1004. In one embodiment, the controller 1070 is configured to control heating of at least one of the segments 1006 and thereby establish and maintain the temperature gradient along the axial direction 1024 of the culture vessel of the bioreactor. Specifically, the controller 1070 is configured to control the one power source 1096a to supply a first power to one heating component 1004a and another power source 1096b to supply a second power to another heating component 1004b along the axial direction 1024 of the heating assembly 1000. The power control enables to establish and maintain the temperature gradient along the axial direction 1024 of the culture vessel of the bioreactor. In one embodiment, the reference signal may be representative of a predetermined value stored in a database. In some other embodiments, the input signal 1072 generated from an adjacent temperature sensor 1098 is representative of the predetermined value.

Specifically, for example, one temperature sensor 1098a is configured to generate an input signal 1072a representative of temperature of one segment 1006a. Another temperature sensor 1098b is configured to generate an input signal 1072b representative of temperature of another segment 1006b. The controller 1070 is configured to receive the input signals 1072a, 1072b and compare the input signals 1072a, 1072b with corresponding reference signals. Thereafter, the controller 1070 is configured to generate a control signal 1074a to regulate the power source 1096a to supply first power to the heating component 1004a. Similarly, the controller 1070 is configured to generate another control signal 1074b to regulate the other power source 1096b to supply second power to the other heating component 1004b. The controller 1070 is configured to generate the plurality of control signals 1074 to maintain a temperature gradient along a side wall of a culture vessel.

Figure 19:
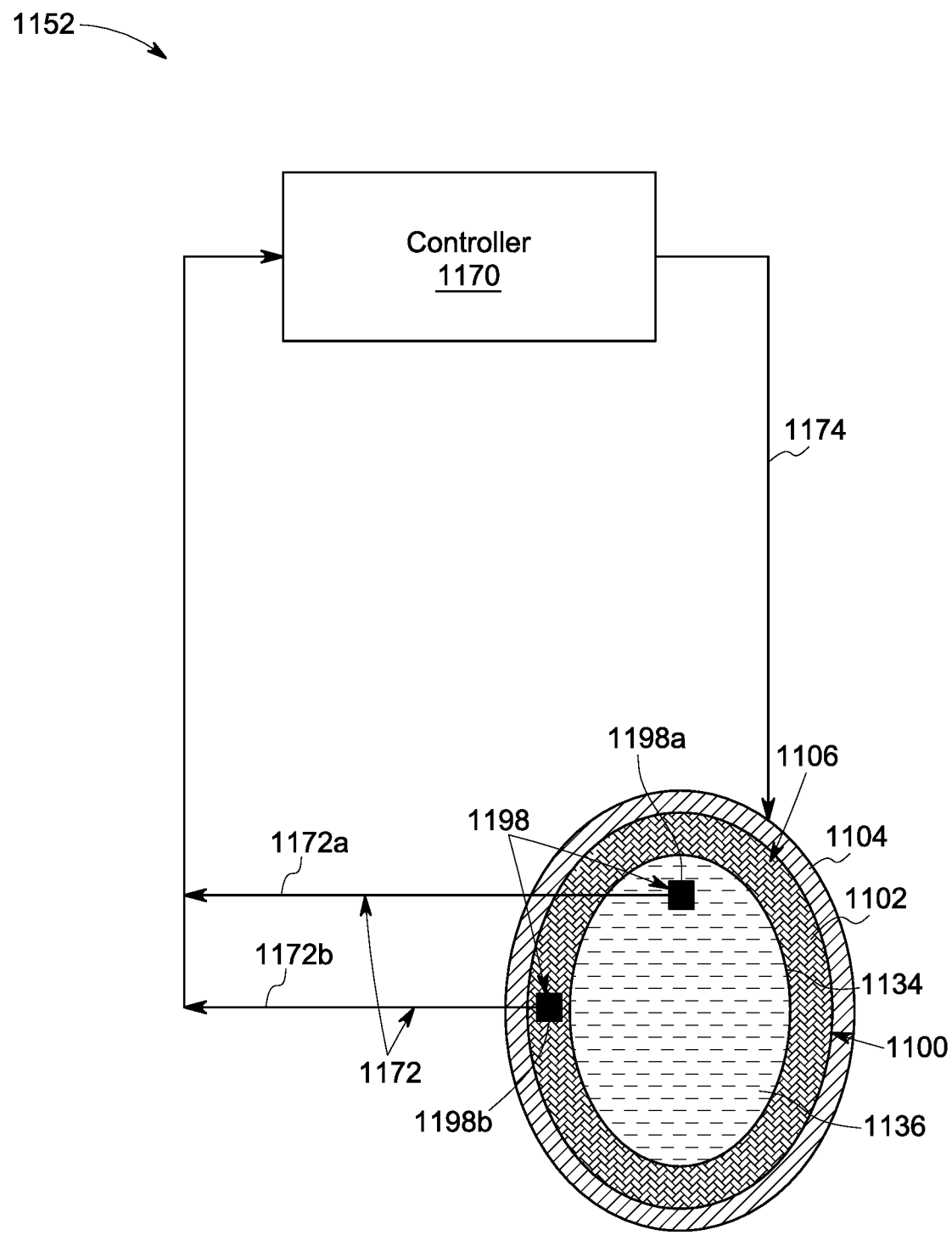
FIG. 19 is a schematic cross-sectional top view of a bioreactor in accordance with another exemplary embodiment.

FIG. 19 illustrates a cross-sectional top view of a bioreactor 1152 in accordance with another exemplary embodiment. The bioreactor 1152 includes a heating assembly 1100 having a holder 1102 and a heating component 1104 which is configured to heat a segment 1106 of the holder 1102. The heating assembly 1100 further includes a plurality of sensors 1198 and a controller 1170 communicatively coupled to the plurality of sensors 1198 and the heating component 1104. Specifically, a first temperature sensor 1198a is disposed in a closed-slot of a culture vessel 1134 (as shown in FIG. 4) to determine temperature of a cell-culture media 1136 disposed within the culture vessel 1134. The first temperature sensor 1198a is configured to generate a first input signal 1172a representative of temperature of the cell-culture media 1136. Further, a second temperature sensor 1198b is disposed on a side wall of the holder 1102 and configured to generate a second input signal 1172b representative of temperature of the segment 1106 of the holder 1102. The controller 1170 is configured to receive the plurality of input signals 1172 and generate a control signal 1174 to regulate the heating of the segment 1106. The heating component 1104 is configured to heat the holder 1102 such that a temperature gradient is maintained along the culture vessel 1134. As a result, water condensation is prevented along an inner surface of the culture vessel and thereby maintaining the plurality of internal parameters at a permissible level conducive for culturing the cells.

In one or more embodiments, establishing and maintaining a temperature gradient is referred to maintaining temperature of the top segment higher than a remaining portion of the side wall. Such a process of establishing and maintaining temperature gradient enables to avoid water condensation at the top segment and at least a portion of bottom segment of the side wall.

Figure 20:
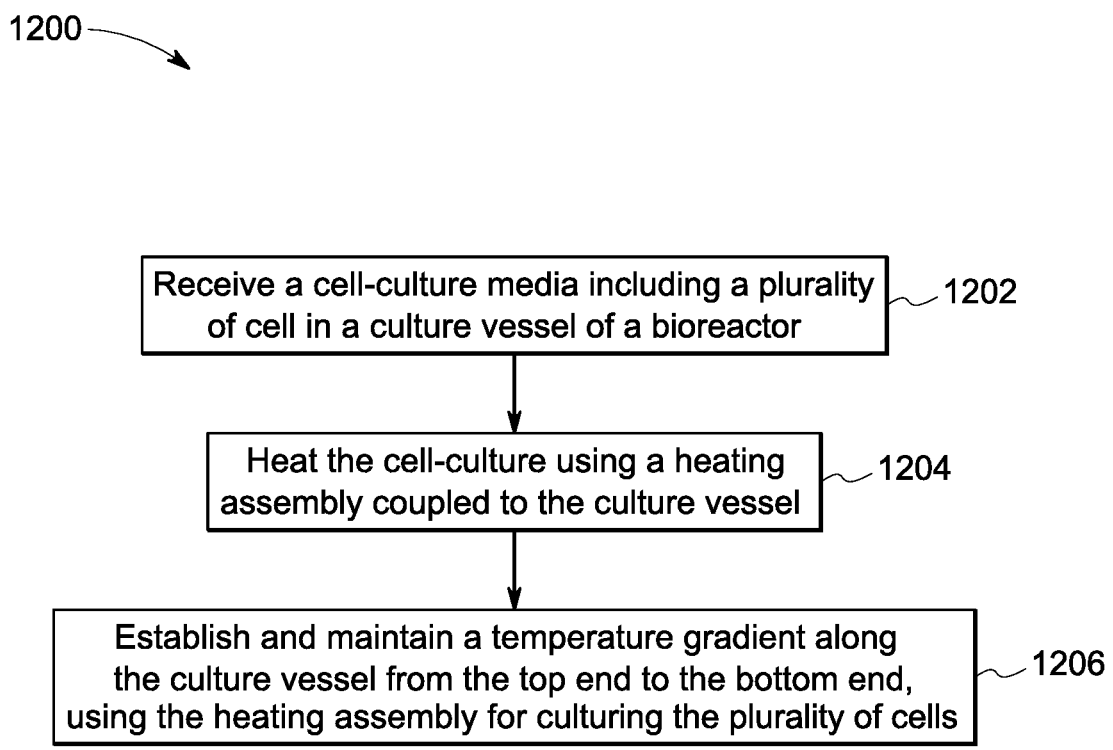
FIG. 20 is a flow diagram of an exemplary method for heating a bioreactor, using a heating assembly in accordance with one exemplary embodiment.

FIG. 20 is a flow diagram of an exemplary method 1200 for heating a bioreactor, using a heating assembly in accordance with one exemplary embodiment.

The method 1200 involves a step 1202 of receiving a cell-culture media including a plurality of cells in a culture vessel of a bioreactor. Specifically, the step 1202 involves the process of transferring the cell-culture media having the plurality of cells into a culture vessel of the bioreactor. In certain embodiments, the cell-culture media is transferred to the culture vessel and the plurality of cells is later transferred to the culture vessel, a using suitable cell transferring device. In one embodiment, the culture vessel is a disposable container having a flower-shaped structure or a conical shaped structure.

The method 1200 further involves a step 1204 of heating the cell-culture media using a heating assembly coupled to the culture vessel. In such embodiments, the culture vessel is disposed within the heating assembly and an outer peripheral surface of the culture vessel conforms to an inner peripheral surface of a unitary structure of the heating assembly. In such embodiments, the heating assembly includes a holder and a heating component. The holder includes a plurality of segments coupled to each other to define the unitary structure. The unitary structure includes a top end, a bottom end, and a side wall extending between the top end and the bottom end. The side wall extends along a circumferential direction of the heating assembly to define a cavity. At least a portion of the unitary structure has a gradually varied perimeter along a direction perpendicular to a plane which intersects the side wall and is parallel to the top end and the bottom end. The heating component is coupled to at least one segment of the plurality of segments.

Further, the method 1200 involves a step of 1206 of establishing and maintaining a temperature gradient along the culture vessel from the top end to the bottom end, using the heating assembly for culturing the plurality of cells.

As discussed, in the embodiments of FIGS. 1-19, establishing and maintaining the temperature gradient along the culture vessel generically includes varying at least one parameter of the unitary structure or varying at least one parameter of the heating component.

In accordance with one or more embodiments discussed herein, an exemplary heating assembly is configured to establish and maintain a temperature gradient along a culture vessel of a bioreactor. Further, the heating assembly prevents water condensation along a side wall of culture vessel by maintaining the temperature gradient along an axial direction of the culture vessel. The unitary structure of the heating assembly enables to maintain a good thermal contact with a culture vessel. A heating component of the heating assembly is made in a form a thin strip thereby improving manufacturability. Further, such a thin strip of the heating component may be easily shaped to conform to various shapes of the unitary structure.

While only certain features of embodiments have been illustrated and described herein, many modifications and changes will occur to those skilled in the art. It is, therefore, to be understood that the appended embodiments are intended to cover all such modifications and changes as falling within the spirit of the invention.

The invention claimed is:

1. A method comprising:
receiving a cell-culture media comprising a plurality of cells in a culture vessel of a bioreactor;
heating the cell-culture media using a heating assembly coupled to the culture vessel, wherein the heating assembly comprises:
a holder comprising a plurality of segments coupled to each other to
define a unitary structure, wherein the unitary structure comprises:
a top end;
a bottom end; and
a side wall extending between the top end and the bottom end and along a circumferential direction of the heating assembly to define a cavity, wherein at least a portion of the unitary structure has a gradually varied perimeter along a direction perpendicular to a plane which intersects the side wall and parallel to the top end and the bottom end; and
a heating component coupled to at least one segment of the plurality of segments; and
establishing and maintaining a temperature gradient along the side wall from the top end to the bottom end using the heating assembly; and
culturing the plurality of cells within the culture vessel at a constant temperature of the cell-culture media while the cell-culture media is exposed to the temperature gradient.

2. The method of claim 1, further comprising controlling heating of at least one segment by the heating component via a controller based on a plurality of inputs signals received from a temperature sensor, wherein the temperature sensor is coupled to the unitary structure, and wherein the controller is coupled to the heating component and the temperature sensor.

3. The method of claim 1, wherein establishing and maintaining the temperature gradient comprises heating the at least one segment comprising the top end, having a uniform perimeter, wherein the heating component is disposed on an outer peripheral surface portion of at least one segment and extends along the circumferential direction of the heating assembly.

4. The method of claim 1, wherein establishing and maintaining the temperature gradient comprises varying a thermal resistance of the unitary structure along an axial direction of the heating assembly, wherein the side wall of the unitary structure has a gradually varied thickness from the top end to the bottom end.

5. The method of claim 1, wherein establishing and maintaining the temperature gradient comprises varying a thermal resistance of the unitary structure along an axial direction of the heating assembly, wherein the side wall of the unitary structure has a gradually varied thermal resistance from the top end to the bottom end.

6. The method of claim 1, wherein establishing and maintaining the temperature gradient comprises varying an amount of heat output by the heating component along an axial direction of the heating assembly, wherein the heating component has a gradually varied thickness from the top end to the bottom end.

7. The method of claim 1, wherein establishing and maintaining the temperature gradient comprises varying an amount of heat output by the heating component along an axial direction of the heating assembly, wherein the heating component is disposed spirally around an outer peripheral surface of the side wall from the top end to the bottom end and wherein the heating component has a gradually varied electrical resistance.

8. The method of claim 1, wherein establishing and maintaining the temperature gradient comprises varying an amount of heat output by the heating component along an axial direction of the heating assembly, wherein the heating component is disposed in a wave-like structure on an outer peripheral surface of the side wall from the top end to the bottom end, along the axial direction of the heating assembly, and wherein the heating component has a gradually varied electrical resistance.

9. The method of claim 1, wherein establishing and maintaining the temperature gradient comprises varying an amount of heat output by the heating component along an axial direction of the heating assembly, wherein the heating component is disposed in a wave-like structure on an outer peripheral surface of the side wall from the top end to the bottom end, along an axial direction of the heating assembly, and wherein the heating component has a gradually varied width from the top end to the bottom end.

10. The method of claim 1, wherein establishing and maintaining the temperature gradient comprises varying an amount of heat output by the heating component along an axial direction of the heating assembly, wherein the heating component is disposed in a wave-like structure on an outer peripheral surface of the side wall from the top end to the bottom end, along an axial direction of the heating assembly, and wherein the heating component comprises a plurality of turns separated from each other by a gap to form a plurality of gradually varied gaps from the top end to the bottom end.

11. The method of claim 1, wherein the heating component comprises a plurality of heating components, wherein each heating component is disposed on a corresponding segment of the plurality of segments and extends along the circumferential direction or an axial direction of the heating assembly, wherein establishing and maintaining the temperature gradient comprises varying an amount of heat output by each of the plurality of heating components along the circumferential direction or the axial direction of the heating assembly, and wherein the plurality of heating components has a gradually varied electrical resistance along the axial direction of the heating assembly.

12. The method of claim 1, wherein the heating component comprises a plurality of heating components, wherein each heating component is disposed on a corresponding segment of the plurality of segments and extends along the circumferential direction or an axial direction of the heating assembly, wherein establishing and maintaining the temperature gradient comprises supplying a first power to one heating component and a second power to another heating component, and wherein the second power is different from the first power.

* * * * *